US007901921B2

(12) United States Patent
Coffey

(10) Patent No.: US 7,901,921 B2
(45) Date of Patent: Mar. 8, 2011

(54) VIRAL PURIFICATION METHODS

(75) Inventor: Matthew C. Coffey, Calgary (CA)

(73) Assignee: Oncolytics Biotech Inc. (CA)

( * ) Notice: Subject to any disclaimer, the term of this patent is extended or adjusted under 35 U.S.C. 154(b) by 667 days.

(21) Appl. No.: 11/255,800

(22) Filed: Oct. 20, 2005

(65) Prior Publication Data

US 2006/0088869 A1    Apr. 27, 2006

Related U.S. Application Data

(60) Provisional application No. 60/621,257, filed on Oct. 22, 2004.

(51) Int. Cl.
 C12N 7/02 (2006.01)
 A61K 39/15 (2006.01)
(52) U.S. Cl. ..................... 435/239; 424/215.1
(58) Field of Classification Search .................. None
 See application file for complete search history.

(56) References Cited

U.S. PATENT DOCUMENTS

| | | | |
|---|---|---|---|
| 4,070,453 A | 1/1978 | Bordt et al. | |
| 4,559,229 A | 12/1985 | Page et al. | |
| 4,721,675 A | 1/1988 | Chan et al. | |
| 5,023,252 A | 6/1991 | Hsei | |
| 5,403,484 A | 4/1995 | Ladner et al. | |
| 5,658,779 A | 8/1997 | Krupey et al. | |
| 5,731,187 A * | 3/1998 | Fanget et al. | 435/235.1 |
| 5,948,441 A | 9/1999 | Lenk et al. | |
| 6,063,384 A | 5/2000 | Morrow et al. | |
| 6,136,307 A | 10/2000 | Lee et al. | |
| 6,143,548 A * | 11/2000 | O'Riordan et al. | 435/239 |
| 6,146,873 A | 11/2000 | Kistner et al. | |
| 6,194,191 B1 | 2/2001 | Zhang et al. | |
| 6,376,210 B1 * | 4/2002 | Yuan | 435/18 |
| 6,528,305 B2 | 3/2003 | Thompson et al. | |
| 6,686,200 B1 * | 2/2004 | Dong et al. | 435/457 |
| 6,726,907 B1 | 4/2004 | Zhang et al. | |
| 6,808,916 B2 | 10/2004 | Coffey et al. | |
| 7,223,585 B2 * | 5/2007 | Coffey | 435/239 |
| 2002/0015945 A1 | 2/2002 | Polo et al. | |
| 2002/0037576 A1 | 3/2002 | Thompson et al. | |
| 2002/0168764 A1 | 11/2002 | Coffey et al. | |
| 2004/0005693 A1 | 1/2004 | Coffey | |
| 2004/0152183 A1 | 8/2004 | O'Riordan et al. | |
| 2004/0241176 A1* | 12/2004 | Lamparski et al. | 424/185.1 |

FOREIGN PATENT DOCUMENTS

| | | |
|---|---|---|
| CA | 2272820 | 5/1998 |
| CA | 2437962 | 9/2002 |
| CA | 2482512 | 11/2003 |
| CA | 2103515 | 2/2004 |
| EP | 0 870 508 | 11/2000 |
| JP | 63044532 A | 2/1988 |
| WO | WO 94/03589 * | 2/1994 |
| WO | 95/24468 | 9/1995 |
| WO | WO 95/31532 | 11/1995 |
| WO | WO 96/15247 | 5/1996 |
| WO | WO 97/08298 | 3/1997 |
| WO | WO 98/22588 | 5/1998 |
| WO | WO 98/26048 | 6/1998 |
| WO | 99/02171 | 1/1999 |
| WO | WO 99/08692 | 2/1999 |
| WO | WO 01/92552 | 12/2001 |
| WO | WO 02/12435 | 2/2002 |
| WO | WO 02/074940 A1 * | 9/2002 |

OTHER PUBLICATIONS

Estes et al. Rotavirus stability and inactivation. J. gen. Virol., 1979, vol. 43, 403-409.*
Henderson et al. Concentration and purification of enteroviruses by membrane chromatography. Applied and Environmental Microbiolgy, No. 1976, Vo. 32, No. 5, 689-693.*
Hagen et al (Biotechnol. Appl. Biochem 23:209-215, 1996; in IDS filed Apr. 2, 2010).*
2002 American Type Culture Collection (ATCC) [on-line], [retrieved on May 16, 2002] Retrieved from the Internet <URL: http://www.atcc.org/SearchCatalogs/longview.cfm>.
Berry et al., "Production of Reovirus Type-1 and Type-3 from Vero Cells Grown on Solid and Macroporous Microcarriers," *Biotechnology and Bioengineering* 62, (1999), pp. 12-19.
Bos, J. L., "Ras Oncogenes in Human Cancer: A Review," *Canc. Res.*, 49(17), pp. 4682-4689 (1989).
Chandron and Nibert, "Protease cleavage of reovirus capsid protein μ1 and μ1C is blocked by alkyl sulfate detergents, yielding a new type of infectious subvirion particle," *J. of Virology*, 72(1), (1998), pp. 467-475.
Coffey, M.C., et al., "Reovirus therapy of tumors with activated Ras pathway," *Science* 282, (1998), pp. 1332-1334.
Drastini, Y., et al., "Comparison of eight different procedures for harvesting avian reoviruses grown in Vero cells," *J. of Virological Methods*, 39, (1992), pp. 269-278.
Drayna et al., "Genetic Studies on the Mechanism of Chemical and Physical Inactivation of Reovirus" *J General Virology* 63(1): 149-160 (1982).
Drayna & Fields, "Biochemical studies on the mechanism of chemical and physical inactivation of reovirus", *Journal of Genetic Virology*, 63(Pt 1):161-170 (1982).
Duncan et al., "Conformational and functional analysis of the C-terminal globular head of the Reovirus cell attachment protein", *Virology* 182(2):810-9 (1991). Estes et al, "Rotavirus stability and inactivation", *J. of Genetic Virology* 43(2): 403-409 (1979).
Floyd and Sharp, "Aggregation of Poliovirus and Reovirus by dilution in water", *Applied and Environmental Microbiology* 33(1): 159-167 (1977).
Floyd and Sharp, Viral aggregation: quantitation and kinetics of the aggregation of poliovirus and reovirus, *Applied and Environmental Microbiology* 35(6): 1079-1083 (1978).
Floyd and Sharp, "Viral aggregation: effects of salts on the aggregation of poliovirus and reovirus at low pH", *Applied and Environmental Microbiology* 35(6): 1084-1094 (1978).
Floyd and Sharp, "Viral aggregation: buffer effects in the aggregation of poliovirus and reovirus at low and high pH", *Applied and Environmental Microbiology* 38(3): 395-401 (1979).

(Continued)

*Primary Examiner* — Mary E Mosher
(74) *Attorney, Agent, or Firm* — McKeon Meunier Carlin Curfman

(57) ABSTRACT

The present invention is directed to an improved method of purifying virus, particularly reovirus. Infectious virus can be extracted from a cell culture with a detergent to produce high titers of virus, and the virus can then be purified by simple steps such as filtration and column chromatography. Viruses and compositions comprising the viruses prepared according to the present invention are also provided.

25 Claims, 8 Drawing Sheets

OTHER PUBLICATIONS

Hand et al., "Reovirus: Analysis of Proteins from Released and Cell-associated Virus", *J. Gen. Virol.*, 12:121-130 (1971).

Hand et al., "Initiation of DNA Replication in Mammalian Cells and its Inhibition of Reovirus Infection", *J. Mol. Biol.*, 82:175-183 (1974).

Hitt, M, et al., "Construction and propagation of human adenovirus vectors", Cell Biology vol. 1, third ed. pp. 500-512 (1998).

Jones, R.C., et al., "Different sensitivities of Vero cells from two sources to avian reoviruses," *Research in Veterinary Science*, 48, (1990), pp. 379-380.

Joklik et al., "What Reassorts When Reovirus Genome Segments Reassort?", *J. Biol. Chem.* 270(9):4181-4184 (1995).

Keirstead et al., "Absence of Super infection exclusion during asynchronous reovirus infections of mouse, monkey, and human cell lines", *Virus Research* 54: 225-235 (1998).

Mah et al., "The N-Terminal Quarter of Reovirus Cell Attachment Protein σ1 Possesses Intrinsic Virion-Anchoring Function", *Virology* 179: 95-103 (1990).

McRae, M.A. and Joklik, W.K., "The nature of the polypeptide encoded by each of the 10 double-stranded RNA segments of reovirus type 3," *Virology*, 89, (1979), pp. 578-593.

Meanger, J., et al., "Immune response to avian reovirus ain chickens and protection against experimental infection," *Aust. Vet. J.*, 75(6), (Jun. 1997), pp. 428-432.

Mendez et al., "A comparative analysis of Freon substitutes in the purification of reovirus and calicivirus", *J. Virological Methods* 90(1): 59-67, 2000.

Mora, M. et al., "Association of reovirus proteins with structural matrix of infected cells", Virology 159: 265-277 (1987).

Nibert et al., "Reoviruses and their replication", *Fundamental Virology* Third Edition, 691-730, 1996.

Nibert et al., "Nonrandom Segregation of Parental Alleles in Reovirus Reassortants", *Journal of Virology* 70(10): 7295-7300 (1996).

Nwajei, B.N.C., et al., "Comparison of chick embryo liver and Vero cell cultures for the isolation and growth of avian reoviruses," *Avian Pathology*, 17, (1988), pp. 759-766.

Onodera, T. et al., "Anti-thyroglobulin antibodies induced with recombinant reovirus infection in BALB/c mice", *Immunology* 71:581-585 (1990).

Poggioli, et al., *J. Virol.*, 74:9562-9570 (2000).

Smith, R.E., et al., "Polypeptide components of virions, top component and cores of reovirus type 3," *Virology*, 39, (1969), pp. 791-810.

Spandidos et al., "Recombination Between Temperature-Sensitive and Deletion Mutants of Reovirus", *J. Virology* 18(1):117-123 (1976).

Spinner and DiGiovanni, "Detection and identification of mammalian Reoviruses in surface water by combined cell culture and reverse transcription-PCR", *Applied and Environmental Microbiology* 67(7): 3016-3020 (2001).

Strong, J.E. and P.W. Lee, "The v-erbV oncogene confers enhanced cellular susceptibility to reovirus infection," *J. Virol.*, 70, (1996), pp. 612-616.

Strong, J.E., et al., "Evidence that the Epidermal Growth Factor Receptor on Host Cells Confers Reovirus Infection Efficiency Virology," 197(1), (1993), pp. 405-411.

Strong, J.E., et al., "The molecular basis of viral oncolysis: usurpation of the Ras signaling pathway by reovirus," *EMBO J.*, 17, (1998), pp. 3351-3362.

Taber et al., "The selection of virus-resistant Chinese hamster ovary cells," *Cell*, 8, (1976), pp. 529-533.

Taylor and Bosmann, "Measurement of the electrokinetic properties of vaccinia and reovirus by laser-illuminated whole-particle microelectrophoresis" *J. of Virology Methods* 2(5): 251-260 (1981).

Turner et al., "Site-Directed Mutagenesis of the C-terminal Portion of Reovirus Protein σ1 Evidence for a Conformaton-Dependent Receptor Binding Domain", *Virology* 186: 219-227 (1992).

Tyler, et al., "Reoviruses," in *Encyclopedia of Virology*, 2$^{nd}$ edition, lines 4-14 on right column of p. 1456 (1999).

Wilcox, G.E., et al., "Adaptation and characteristics of replication of a strain of avian reovirus in Vero cells," *Avian Pathology*, 14, (1985), pp. 321-328.

Vellekamp et al., "Empty Capsids in Column-Purified Recombinant Adenovirus Preparations", *Human Gene Therapy* 12: 1923-1936 (2001).

Wyatt R.G. et al., "Probable in vitro cultivation of human reovirus like agent of infantile diarrhoea," *Lancet* (1976) 1/7950:98-99.

Zerda et al., "Adsorption of viruses to charge-modified silica", *Applied and Environmental Microbiology* 49(1): 91-95 (1985).

Mertens, P.P.C., Burroughs, J.N., Anderson, J., "Purification and Properties of Virus Particles, Infectious Subviral Particles, and Cores of Bluetongue Virus Serotypes 1 and 4" *Virology* 157:375-386 (1987).

Crossley, L.; "Membrane Chromatography: Not Just for Viral Clearance Anymore?" www.wpi.edu/Images/CMS/BEI/lisacrossley.pdf; Feb. 20, 2007, WPI Bioengineering Institute Symposium: New Developments in Biomanufacturing.

Hartwig et al., "Topical treatment of ocular surface defects: comparison of the epitheliotrophic capacity of fresh frozen plasma and serum on corneal epithelial cells in an in vitro cell culture model." *Transfusion Medicine*, 15:107-113 (2005).

Liu et al., "Corneal Epitheliotrophic Capacity of Three Different Blood-Derived Preparations." *Investigative Opthamalogy and Visual Science*, 47(6): 2438-2444 (2006).

Nooteboom et al., "Modulation of endothelial monolayer permeability induced by plasma obtained from lipopolysaccharide-stimulated whole blood." *Clinical and Experimental Immunology*, 144:362-369 (2006).

Wallis et al., "Enterovirus concentration on cellulose membranes." *Applied Microbiology* 23:476-480 (1972).

Wallis et al., "Concentration of enteroviruses on membrane filters." *Journal of Virology* 1:472-477 (1967).

Hagen et al., "Use of a nuclease enzyme in the purification of VAQTA®, a hepatitis A vaccine," *Biotechnol. Appl. Biochem.* 23, 209-215 (1996).

Communication of a notice of opposition issued in European Application No. 03724692.3 on Jan. 25, 2010; available online on Jan. 12, 2010.

Wang et al., "Natural Supramolecular Building Blocks: Wild-Type Cowpea Mosaic Virus," Chemistry & Biology, 9 (7):805-811 (2002).

Second Office Action issued in Chinese Application No. 200580044412.4 on Apr. 14, 2010.

Henderson et al., "Concentration and Purification of Enteroviruses by Membrance Chromatography," Applied and Environmental Microbiology, Nov. 1976, vol. 32, No. 5, pp. 689-693. ISSN 0099-2240.

\* cited by examiner

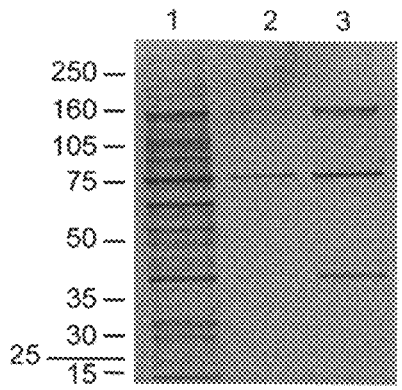
FIG. 8A
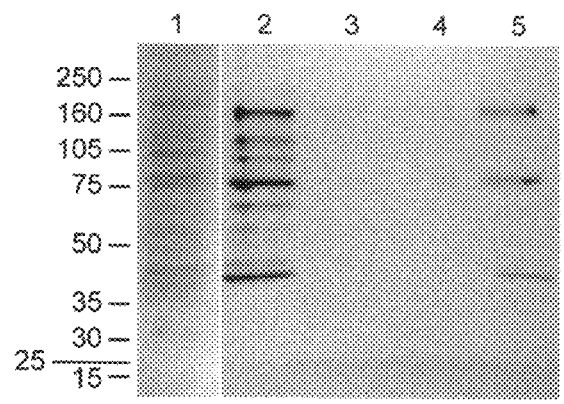
FIG. 8B
| Sample | Corrected Titer ± 95% PFU/ml CI (Log10TCID50ml) | | Corrected for ml Appl./Collect | Yield |
|---|---|---|---|---|
| UF/DF Material | 9.91 ± 0.21 | $1.225 \times 10^{10}$ | n.a. | 100% |
| Q Sepharose HP Capacity Study | 10.57 ± 0.21 | $3.72 \times 10^{10}$ | 10 CV Applied, Collect in 2.5 CV | 76% |
| Q Sepharose HP | 10.98 ± 0.21 | $9.55 \times 10^{10}$ | 10 CV Applied (78.5 ml) 6 ml Collect ($5.73 \times 10^{11}$) | 59.68% |
| SEC Scale Up | 10.80 ± 0.31 | $6.31 \times 10^{10}$ | 5.1 ml Applied 5.823 ml Collected | 78.50% |
FIG. 8C

VIRAL PURIFICATION METHODS

CROSS-REFERENCE TO RELATED APPLICATIONS

This application is a non-provisional application claiming benefit of U.S. Patent Application No. 60/621,257, filed Oct. 22, 2004, the entire disclosure of which is incorporated herein by reference in its entirety.

TECHNICAL FIELD

This invention relates to a method of extracting virus from a cell culture. In particular, the method is useful for extracting infectious virus in a form which is suitable for clinical administration to mammals, including humans.

REFERENCES

U.S. Patent Application Publication No. 20020037576, published Mar. 28, 2002.
WO99/08692A1, published Feb. 25, 1999.
Japanese Patent 63044532A, published Feb. 25, 1988.
Berry et al., Biotechnology and Bioengineering, "Production of Reovirus Type-1 and Type-3 from Vero Cells Grown on Solid and Macroporous Microcarriers", *Biotechnology and Bioengineering* 62: 12-19 (1999).
Bos, J. L., "Ras Oncogenes in Human Cancer: A Review", *Canc. Res.* 49(17): 4682-4689 (1989).
Chandron and Nibert, "Protease cleavage of reovirus capsid protein mu1 and mu1C is blocked by alkyl sulfate detergents, yielding a new type of infectious subvirion particle", *J. of Virology* 72(1):467-75 (1998).
Coffey, M. C., et al., "Reovirus therapy of tumors with activated Ras pathway", *Science* 282: 1332-1334 (1998).
Davis, et al., *Microbiology*, Lippincott, Philadelphia (1990).
Drastini, Y. et al., "Comparison of eight different procedures for harvesting avian reoviruses grown in Vero cells", *J. Virological Methods* 39: 269-278 (1992).
Drayna D. and Fields B. N., "Biochemical studies on the mechanism of chemical and physical inactivation of reovirus", *Journal of Genetic Virology* 63(Pt 1):161-170 (1982).
Duncan et al., "Conformational and functional analysis of the C-terminal globular head of the reovirus cell attachment protein", *Virology* 182(2):810-9 (1991).
Estes M. K. et al, "Rotavirus stability and inactivation", *J. of Genetic Virology* 43(2):403-409 (1979).
Floyd R. and Sharp D. G., "Aggregation of poliovirus and reovirus by dilution in water", *Applied and Environmental Microbiology* 33(1):159-167 (1977).
Floyd R. and Sharp D. G., "Viral aggregation: quantitation and kinetics of the aggregation of poliovirus and reovirus", *Applied and Environmental Microbiology* 35(6):1079-1083 (1978).
Floyd R. and Sharp D. G., "Viral aggregation: effects of salts on the aggregation of poliovirus and reovirus at low pH", *Applied and Environmental Microbiology* 35(6):1084-1094 (1978).
Floyd R. and Sharp D. G., "Viral aggregation: buffer effects in the aggregation of poliovirus and reovirus at low and high pH", *Applied and Environmental Microbiology* 38(3):395-401 (1979).
Fields, B. N. et al., *Fundamental Virology, 3rd Edition*, Lippincott-Raven (1996).
Mah et al., "The N-terminal quarter of reovirus cell attachment protein sigma 1 possesses intrinsic virion-anchoring function", *Virology* 179(1):95-103 (1990).
McRae, M. A. and Joklik, W. K., "The nature of the polypeptide encoded by each of the 10 double-stranded RNA segments of reovirus type 3", *Virology*, 89:578-593 (1979).
Nibert et al., "Reovirus and their replication", in Fields et al., *Fundamental Virology, 3rd Edition*, Lippincott-Raven (1996).
*Remington's Pharmaceutical Sciences*, Mack Publishing Company, Philadelphia Pa. 19.sup.th ed. (1995).
Smith, R. E., et al., "Polypeptide components of virions, top component and cores of reovirus type 3", *Virology*, 39:791-800 (1969).
Spinner M. L. and DiGiovanni G. D., "Detection and identification of mammalian reoviruses in surface water by combined cell culture and reverse transcription-PCR", *Applied and Environmental Microbiology* 67(7):3016-3020 (2001).
Strong, J. E. and P. W. Lee, "The v-erbV oncogene confers enhanced cellular susceptibility to reovirus infection", *J. Virol.* 70: 612-616 (1996).
Strong, J. E., et al., "Evidence that the Epidermal Growth Factor Receptor on Host Cells Confers Reovirus Infection Efficiency", *Virology* 197(1): 405-411 (1993).
Strong, J. E., et al., "The molecular basis of viral oncolysis: usurpation of the Ras signaling pathway by reovirus", *EMBO J.* 17: 3351-3362 (1998).
Taber et al., "The selection of virus-resistant Chinese hamster ovary cells", *Cell* 8: 529-533 (1976).
Taylor D. H. and Bosmann H. B., "Measurement of the electrokinetic properties of vaccinia and reovirus by laser-illuminated whole-particle microelectrophoresis", *J. of Virology Methods* 2(5):251-260 (1981).
Turner and Duncan, "Site directed mutagenesis of the C-terminal portion of reovirus protein sigma1: evidence for a conformation-dependent receptor binding domain", *Virology* 186(1):219-27 (1992).
Zerda K. S. et al, "Adsorption of viruses to charge-modified silica", *Applied and Environmental Microbiology* 49(1): 91-95 (1985).

All of the publications, patents and patent applications cited above or elsewhere in this application are herein incorporated by reference in their entirety to the same extent as if the disclosure of each individual publication, patent application or patent was specifically and individually indicated to be incorporated by reference in its entirety.

BACKGROUND

Due to the vast number of diseases caused by viruses, virology has been an intensively studied field. There has always been the demand to produce viruses efficiently in order to isolate and purify viral proteins, to generate vaccines, or to provide infectious viruses for laboratory studies. Recently, the new development of virus therapy has further necessitated the need for efficient production of infectious viruses.

Reovirus therapy is an example of virus therapy. Reovirus is a double-stranded RNA virus capable of binding to a multitude of cells. However, most cells are not susceptible to reovirus infection and binding of reovirus to its cellular receptor results in no viral replication or virus particle production in these cells. This is probably the reason why reovirus is not known to be associated with any particular disease.

Cells transformed with the ras oncogene become susceptible to reovirus infection, while their untransformed counterparts are not (Strong et al., 1998). For example, when reovirus-resistant NIH 3T3 cells were transformed with activated Ras or Sos, a protein which activates Ras, reovirus infection was enhanced. Similarly, mouse fibroblasts that are resistant to reovirus infection became susceptible after transfection with the EGF receptor gene or the v-erbB oncogene, both of which activate the ras pathway (Strong et al., 1993; Strong et al., 1996). Thus, reovirus can selectively infect and replicate in cells with an activated Ras pathway.

The ras oncogene accounts for a large percentage of mammalian tumors. Activating mutations of the ras gene itself occur in about 30% of all human tumors (Bos, 1989), primarily in pancreatic (90%), sporadic colorectal (50%) and lung (40%) carcinomas, as well as myeloid leukemia (30%). Activation of factors upstream or downstream of ras in the ras pathway is also associated with tumor. For example, overexpression of HER2/Neu/ErbB2 or the epidermal growth factor (EGF) receptor is common in breast cancer (25-30%), and overexpression of platelet-derived growth factor (PDGF) receptor or EGF receptor is prevalent in gliomas and glioblastomas (40-50%). EGF receptor and PDGF receptor are both known to activate ras upon binding to their respective ligand, and v-erbB encodes a constitutively activated receptor lacking the extracellular domain.

Since a large number of human tumors are accounted for by genetic alteration of the proto-oncogene ras or a high Ras activity, reovirus therapy is a new, promising therapy for such conditions (Coffey et al., 1998). Reovirus therapy is highly selective for Ras-associated tumor cells and leaves normal cells uninfected. This therapy has wide applications and can be used in both human and non-human animals.

In order to produce reovirus suitable for clinical administration, fast and efficient methods of producing reovirus in cultured cells are needed. Moreover, the traditional method of purifying viruses from cultured cells is tedious and time consuming, rendering the cost of virus production too high. Therefore, an improved method for virus purification is also needed.

SUMMARY OF THE INVENTION

The present invention relates to an improved method of extracting and purifying viruses from cell culture that can be applied to both small and large scale virus production. The method involves a simple extraction step in which a detergent is directly added to the cell culture. Thereafter, cell debris can be removed from the extraction mixture by, for example, filtration or centrifugation. The resulting virus suspension can be further concentrated and/or enriched by chromatographic methods. The virus prepared according to the present invention can be used for any purpose, including purification of viral proteins, vaccination, infection of host cells and clinical administration.

Accordingly, one aspect of the present invention provides a method of producing virus from a culture of cells, comprising the steps of:
(a) providing a culture of cells which has been infected by the virus;
(b) extracting the virus from the cells by adding a detergent to the culture and incubating for a period of time to result in a cell lysate;
(c) removing cell debris; and
(d) collecting the virus.

Any method can be used to remove cell debris (i.e., clarify the cell lysate) in step (c). The method is preferably a simple method based on the size or density differences between the virus and the other constituents in the cell lysate (e.g., filtration or centrifugation). More preferably, filtration is employed, particularly step-wise filtration. An appropriate step-wise filtration comprises a prefilter having a larger pore size, followed by at least another filter with a pore size smaller than that of the prefilter. In a preferred embodiment, the cell debris is removed by step-wise filtration comprising:
(1) filtering through a prefilter having a pore size of 5 µM or 8 µM, and
(2) filtering after step (1) through a combination filter having pore sizes of 3 µM and 0.8 µM.

In another preferred embodiment, step (2) above comprises filtering after step (1) through a filter having a pore size of 0.8 µM.

The cell lysate can optionally be treated with BENZONASE® endonuclease or other DNA-cleaving enzyme to break up long, viscous cellular DNA. After removing cell debris by filtration, the filtrate can optionally be concentrated to reduce the volume of the viral suspension. Any methods suitable for viral concentration can be employed, preferably ultrafiltration or diafiltration, including tangential flow filtration. Exemplary methods include the Plate and Frame system and the Hollow Fiber system. More preferably, the Hollow Fiber system is used. In a preferred embodiment, diafiltration with the Hollow Fiber system comprises using a hollow fiber cartridge having a molecular weight cut-off of 300 kDa.

The present method can be applied in the production of any virus, preferably a non-enveloped virus, and most preferably a reovirus. The reovirus is preferably a mammalian reovirus, more preferably a human reovirus, still more preferably a serotype 3 reovirus, and most preferably a Dearing strain reovirus. The reovirus may be a recombinant reovirus. The recombinant reovirus may be generated by co-infection of cells, such as mammalian cells or avian cells, with different subtypes of reovirus. The recombinant reovirus may be naturally-occurring or non-naturally-occurring. The recombinant reovirus may be from two or more strains of reovirus, particularly two or more strains of reovirus selected from the group consisting of strain Dearing, strain Abney, strain Jones, and strain Lang. The recombinant reovirus may also result from reassortment of reoviruses from different serotypes, such as selected from the group consisting of serotype 1 reovirus, serotype 2 reovirus and serotype 3 reovirus. The recombinant reovirus may comprise naturally-occurring variant coat protein coding sequences or mutated coat protein coding sequences.

The cell culture used in the present invention can comprise any cell appropriate for the production of the desired virus. For reovirus, the cell is preferably human embryo kidney 293 (HEK 293) cells or cells derived therefrom, particularly HEK 293 cells that have been adapted to grow in suspension cultures.

The method can optionally comprise a step of ion exchange chromatography, wherein the virus is enriched by binding to an ion exchange resin under appropriate conditions. The virus is then eluted from the ion exchanger using a suitable elution solution. The choice of ion exchanger and binding/elution conditions will vary with the virus being purified. For reovirus, an anion exchanger and pH of approximately 7.0-9.0 are the most effective. The pH is preferably about 7.5 to about 8.5, and most preferably about 8.0. Preferably, the ion exchange is performed in a phosphate buffer, such as 50 mM sodium phosphate, pH 7.2. The binding/elution buffer is preferably free of magnesium salts.

The virus can also be purified by using size exclusion chromatography. The size exclusion chromatography is preferably carried out in a phosphate buffer, such as 50 mM sodium phosphate, pH 7.2. Additionally, size exclusion chromatography can be carried out in the absence of magnesium salts. In particular, a combination of ion exchange and size exclusion chromatography can be employed. In one embodiment, reovirus is purified using an anion exchanger followed by size exclusion chromatography.

Another aspect of the present invention provides a composition comprising the virus purified according to any of the methods described herein. The composition is preferably suitable for clinical administration, particularly clinical administration to humans. More preferably, the composition comprises a pharmaceutically acceptable excipient and/or carrier.

Another aspect of the present invention provides a method of producing infectious reovirus, comprising:
(a) providing a culture of HEK 293 cells which has been infected by reovirus;
(b) extracting the virus from the cells by adding TRITON® X-100 (octoxynol-9 to 10) to the culture and incubating at about 25° C. to about 37° C.;
(c) treating the mixture from step (b) with BENZO-NASE™ endonuclease;
(d) removing cell debris by filtration;
(e) concentrating the filtrate by ultrafiltration or diafiltration;
(f) purifying the reovirus by a combination of ion exchange and size exclusion chromatography; and
(g) collecting the reovirus.

Also provided are compositions comprising the reovirus collected according to this method, particularly compositions further comprising a pharmaceutically acceptable excipient and/or carrier.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 8A shows a silver stained 4-12% SDS PAGE gel of: lane 1: virus fraction after Q Sepharose HP purification, lane 2 CsCl purified standard, lane 3: SEC purified final material diluted 2 fold.

FIG. 8B shows a 4-12% SDS PAGE coomassie stained gel of the purification procedure. Lane 1, starting material, lane 2 Q Sepharose material, lane 3 CsCl material diluted 2×, lane 4 CsCl material undiluted, lane 5 SEC purified material.

FIG. 8C is a table of the reovirus recoveries as determined by TCID50.

DETAILED DESCRIPTION OF THE INVENTION

Figure 1:
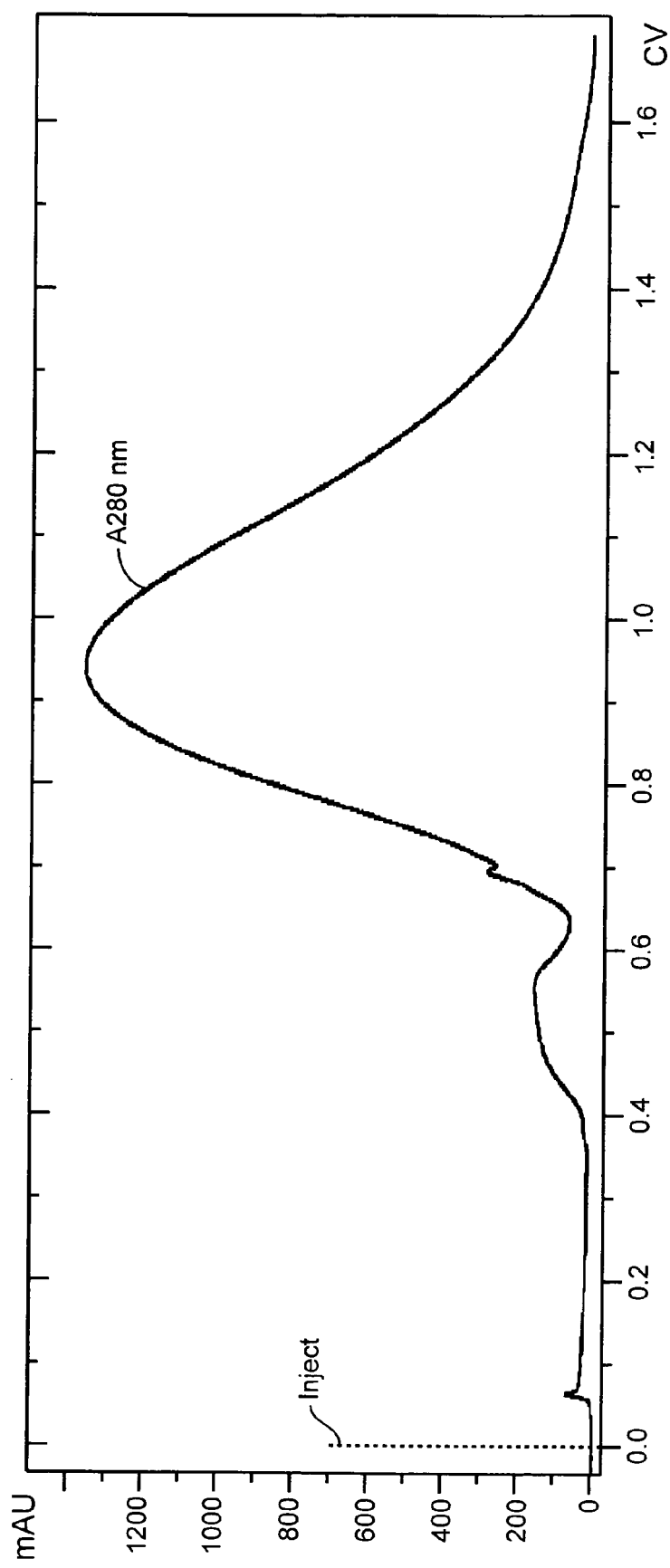
FIG. 1 shows separation of the reovirus ultrafiltration/diafiltration (UF/DF) material at 150 cm/h. The material was buffer exchanged into 50 mM phosphate pH 7.2, 5% glycerol on an HR5__200 Sepharose 4 Fast Flow column. 0.30 CV of sample were applied. The void volume, eluting from 0.37 CV-0.62 CV was collected. x-axis in CV; y-axis in milli-absorption units at 280 nm.

The present invention relates to an improved method of extracting and purifying viruses from cell culture that can be applied to both small and large scale virus production. The method involves a simple extraction step in which a detergent is directly added to the cell culture. Thereafter, cell debris can be removed from the extraction mixture by, for example, filtration or centrifugation. The resulting virus suspension can be further concentrated and/or enriched by chromatographic methods. The virus prepared according to the present invention can be used for any purpose, including purification of viral proteins, vaccination, infection of host cells and clinical administration.

Prior to describing the invention in further detail, the terms used in this application are defined as follows unless otherwise indicated.

Definitions

As used herein, "adherent cells" refer to cells which adhere to the culture containers in a cell culture. Examples of adherent cells include monolayer cells, which are cells that form a single layer of cells on the surface of a culture container. "Suspension cells" or "suspended cells" refer to cells which do not adhere to culture containers in a cell culture. Suspension cells can be grown in a "spin culture", which is a culture in which the culture medium is stirred continuously during the culture process.

As used herein, "ambient temperature" refers to a temperature between about 10° C. and about 30° C. Ambient temperature is preferably between about 15° C. and about 30° C., more preferably between about 20° C. and about 25° C., and most preferably about 25° C.

As used herein, a virus that is "cell associated" refers to a virus which is attached to or trapped in part of a cell in which the virus has been produced. Thus, a virus is cell associated before the host cell is lysed. When cell lysis begins, a virus may be still attached to or trapped in part of the broken cell and remain cell associated. However, when the virus is released free into the medium, it is not cell associated anymore. A "cell free virus" is a virus which is not cell associated.

As used herein, a "cell culture" or "culture of cells" means a population of cultured cells as found in their culture conditions. In particular, a cell culture includes the cells and the culture medium. Cells that have been pelleted are not considered a cell culture unless they are placed in culture medium under culture conditions again.

As used herein, "cell lysis" refers to the disruption of the cell membrane of a cell and the subsequent release of all or part of the content of the cell.

As used herein, "clinical administration" of a substance refers to contacting any part of the body of a living organism with the substance in order to improve or maintain the organism's health conditions.

As used herein, "collecting" the virus refers to the act of separating the virus produced from a cell culture which has been previously infected with the virus. The virus is typically collected by separating cellular debris from the virus and harvesting the portion which comprises the virus. Optionally, the virus can be further separated from the soluble substances, e.g., by centrifugation.

As used herein, "culture conditions" refer to the conditions used in a cell culture, including but not limited to the temperature, type of culture containers, humidity, concentration of $CO_2$ or any other gas used in the culture containers, type of culture medium, the initial density of the cultured cells, and, if the cells are infected with a virus, the initial multiplicity of infection.

As used herein, "cytopathic effect" is the damage to infected host cells. Cytopathic effect may be indicated by cells becoming swollen and granular in appearance and cell clumps breaking up. Cells which show a cytopathic effect may also take up the staining dye in a viable cell count.

As used herein, a "detergent" is a substance having a hydrophilic moiety and a hydrophobic moiety. The detergent is preferably a synthetic chemical compound and more preferably a biodegradable synthetic chemical compound. A detergent useful in the present invention enhances disruption of cell membranes to facilitate release of the content of the disrupted cells.

As used herein, a cell is "disrupted" when the cell membrane is ruptured and at least some of the cell content is released from the cell. A cell may be disrupted, for example, by freeze-thawing, sonication or detergent treatments.

As used herein, "extracting" a virus refers to the act of converting a cell associated virus into a cell free virus.

As used herein, "HEK 293 cells" refer to the human embryo kidney cell line designated 293 (ATCC Number CRL-1573) or its derivatives. For example, 293/SF cells (ATCC Number CRL-1573.1) are HEK 293 cells which have been adapted to grow in serum-free media. Also contemplated in this invention are HEK 293 cells adapted to grow in other culture conditions, or any kind of HEK 293 cells or derivatives which are transformed with an exogenous DNA, provided that this transformation does not impair the ability of the cells to support efficient reovirus production as described in this invention.

As used herein, "incubating" after addition of a detergent to a cell culture refers to the act of allowing the cell culture to be mixed with the detergent for a period of time.

As used herein, "multiplicity of infection" or "MOI" refer to the ratio of the number of virus to the number of cells when a virus is used to contact cells.

As used herein, a "non-enveloped virus" is a virus which does not have an envelope. For example, a non-enveloped virus may be any virus which belongs to the family of Adenoviridae (e.g. adenovirus), Picornaviridae (e.g. polio virus), Reovirudae (e.g. reovirus), Papovarviridae (e.g. papilloma virus), Parvoviridae (e.g. Kilham rat virus) or Iridoviridae (e.g. tipula iridescent virus).

As used herein, "reovirus" refers to any virus classified in the reovirus genus, whether naturally occurring, modified or recombinant. Reoviruses are viruses with a double-stranded, segmented RNA genome. The virions measure 60-80 nm in diameter and possess two concentric capsid shells, each of which is icosahedral. The genome consists of double-stranded RNA in 10-12 discrete segments with a total genome size of 16-27 kbp. The individual RNA segments vary in size. Three distinct but related types of reovirus have been recovered from many species. All three types share a common complement-fixing antigen.

The human reovirus consists of three serotypes: type 1 (strain Lang or T1L), type 2 (strain Jones, T2J) and type 3 (strain Dearing or strain Abney, T3D). The three serotypes are easily identifiable on the basis of neutralization and hemagglutinin-inhibition assays (see, for example, Fields, B. N. et al., 1996).

The reovirus may be naturally occurring or modified. The reovirus is "naturally-occurring" when it can be isolated from a source in nature and has not been intentionally modified by humans in the laboratory. For example, the reovirus can be from a "field source", that is, from a human who has been infected with the reovirus.

The reovirus may be a recombinant reovirus resulting from the recombination/reassortment of genomic segments from two or more genetically distinct reoviruses. Recombination/reassortment of reovirus genomic segments may occur in nature following infection of a host organism with at least two genetically distinct reoviruses. Recombinant virions can also be generated in cell culture, for example, by co-infection of permissive host cells with genetically distinct reoviruses (Nibert et al. 1995).

Accordingly, the invention contemplates the recombinant reovirus resulting from reassortment of genome segments from two or more genetically distinct reoviruses, including but not limited to, human reovirus, such as type 1 (e.g., strain Lang), type 2 (e.g., strain Jones), and type 3 (e.g., strain Dearing or strain Abney), non-human mammalian reoviruses, or avian reovirus. The invention further contemplates recombinant reoviruses resulting from reassortment of genome segments from two or more genetically distinct reoviruses wherein at least one parental virus is genetically engineered, comprises one or more chemically synthesized genomic segment, has been treated with chemical or physical mutagens, or is itself the result of a recombination event. The invention further contemplates the recombinant reovirus that has undergone recombination in the presence of chemical mutagens, including but not limited to dimethyl sulfate and ethidium bromide, or physical mutagens, including but not limited to ultraviolet light and other forms of radiation.

The invention further contemplates recombinant reoviruses that comprise deletions or duplications in one or more genome segments, that comprise additional genetic information as a result of recombination with a host cell genome, or that comprise synthetic genes.

The reovirus may be modified by incorporation of mutated coat proteins, such as for example σ1, into the virion outer capsid. The proteins may be mutated by replacement, insertion or deletion. Replacement includes the insertion of different amino acids in place of the native amino acids. Insertions include the insertion of additional amino acid residues into the protein at one or more locations. Deletions include deletions of one or more amino acid residues in the protein. Such mutations may be generated by methods known in the art. For example, oligonucleotide site directed mutagenesis of the gene encoding for one of the coat proteins could result in the generation of the desired mutant coat protein. Expression of the mutated protein in reovirus infected mammalian cells in vitro such as COS1 cells will result in the incorporation of the mutated protein into the reovirus virion particle (Turner and Duncan, 1992; Duncan et al., 1991; Mah et al., 1990).

As used herein, "viability of the cells" or "percentage of cells remaining viable" is the percentage of the cells which do not show a cytopathic effect in a population.

As used herein, "viral infection" refers to the entry of a virus into a cell and the subsequent replication of the virus in the cell.

Methods

We have previously developed a method of growing reovirus in HEK 293 cells (U.S. Patent Application Publication No. 20020037576). Reovirus replicates in HEK 293 cells to yield a high titer of virus in the cells shortly after virus infection, thereby providing a simple and efficient method of producing reovirus. In addition, HEK 293 cells has been adapted to grow in suspension which can be cultured in large quantity, and we developed a large scale production method. To isolate reovirus from the suspension culture, we initially followed traditional methods to extract and purify viral particles. Briefly, the cells were disrupted by freeze-thawing and extracted by FREON® (1,1,2-trichloro-1,1,2-trifluoro-ethane) three times. The viral particles were then purified with a CsCl gradient and ultracentrifugation. However, this protocol was too tedious and time consuming for large scale virus production.

We therefore developed a simplified method to extract the reovirus. It was discovered that by incubating the HEK 293 cell culture with a detergent for a short period of time, high levels of infectious reovirus were released to the extract. The virus can then be separated from the cell debris with a simple separation method based on size or density differences, such as filtration, diafiltration or size exclusion, and the resulting virus can be used for reovirus therapy. The reovirus produced according to the present invention is suitable for administration in humans, and this protocol is consistent with the FDA recommendation of disrupting cells in the presence of a detergent.

We tested four detergents in a preliminary experiment, the non-ionic detergents octoxynol-9 to 10 (TRITON® X-100), octylphenoxy polyethoxy ethanol (NONIDET™ P40 or NP-40) and polyethylene glycol sorbitan monolaurate (TWEEN® 20), as well as the ionic detergent sodium deoxycholate. All four detergents were capable of lysing the cells and releasing infectious viral particles above the background level, and TRITON® X-100 was the most effective. It is contemplated that other detergents, particularly the ones commonly used to disrupt cells, can be used in the present invention as well. Examples of these other detergents include the other TRITON® detergents, the other TWEEN® detergents (e.g., polyoxyethylene sorbitan monooleate TWEEN® 80), sodium dodecyl sulfate, lithium dodecyl sulfate, and dodecyltrimethylammonium chloride.

The results also indicate that detergent extraction can be more effective than freeze-thawing, the standard procedure for virus extraction. In addition, it has been reported that to extract avian reovirus from Vero cells in which the reovirus is highly cell associated, distilled deionized water was more effective than freeze-thawing, FREON® (1,1,2-trichloro-1, 1,2-trifluoro-ethane) extraction or trypsin treatment (Drastini et al., 1992). The present invention provides a more rapid and convenient yet effective approach, because there is no need to pellet and then resuspend the cells as required by the distilled water method.

It is contemplated that high concentrations of salt, such as guanidine chloride, can be used in the present invention to substitute for detergents. However, it is preferable to use detergents rather than high concentrations of salt.

The present invention thus provides a fast and simple method of extracting viruses from a cell culture. The detergent can be added directly to a suspension culture or to the medium of adherent cells. In either case, the medium does not need to be removed first. Furthermore, no other means of disrupting cells or extracting viruses is necessary, such as freeze-thawing or sonication.

An important feature of the present invention is that the extraction procedure can be performed at or above ambient temperature. Traditionally, virus extraction and purification are carried out at a low temperature, typically 0-4° C., to preserve the structures and functions of proteins. For the same reason, protease inhibitors are usually also included in the extraction solutions. Therefore, it is surprising that the present protocol can be conducted at a higher temperature without any protease inhibitor. In fact, a temperature as high as 37° C. resulted in about the same amount of infectious virus as temperatures of 25° C. Consequently, virus extraction can be carried out by adding a detergent directly to the cell culture and continuing to agitate the culture in order to release the virus, without having to change the temperature. Alternatively, since there is no need to maintain a constant temperature for virus extraction according to the present invention, the procedure can take place at ambient temperature even though ambient temperature may vary from place to place or with time in the same place.

Subsequent to extraction, the virus can be purified based on, for example, the size or density difference between the virus and the other constituents in the extract. Particularly, filtration or centrifugation can be employed to remove cell debris from the virus. To optimize filtration conditions, we tested the effect of various filters in the presence of several different extraction detergents (Example 1). A step-wise filtration protocol proved to be the most effective. Thus, a pre-filter having a relatively large pore size (e.g., 5 μM or 8 μM) is first used to remove large pieces from the extraction mixture, followed by filters with small pore sizes, such as a combination filter unit containing a 3 μM filter and a 0.8 μM filter. In the absence of pre-filters, the extraction mixture would clog the filter quickly, thereby wasting both material and time. In another embodiment, after the 5 μM or 8 μM pre-filter step, a filter having a single pore size of 0.8 μM can be used.

Based on the volume collected after filtration, as shown in Example 1, it is preferable to use 1% TRITON® X-100 for virus extraction. In addition, cellulose acetate membrane filters are better than glass fiber membrane filters, because the cellulose acetate membrane filter allows a higher volume of extraction mixture to be filtered, rendering it more suitable for large-scale production.

Depending on the purpose of virus production, it may be desirable to concentrate the virus-containing filtrate. A concentration step using ultrafiltration/diafiltration is demonstrated in Examples 2 and 4. In Example 2, two ultrafiltration/diafiltration systems were tested, the Plate and Frame Cassette of Pall Filtron and the Hollow Fiber Cartridge of A/G Technology. The results show that the two systems are comparable in their speed of operation or the extent of volume loss, but the Hollow Fiber Cartridge is easier to handle. In Example 4, the results show that a Hollow Fiber Cartridge having a molecular cut-off of 300 kDa provided good material for subsequent purification.

The virus may be further purified based on its surface charge. Since different viruses have different surface proteins, which dictate their surface charge at any given pH, the appropriate condition for purification will have to be decided for each virus. Example 3 illustrates a determination of optimal ion exchange conditions for reovirus. Thus, ion exchange columns containing different resins were used at different pH to purify a reovirus preparation that had been extracted, filtered and concentrated as described above. The results indicate that a weak anion column containing ANX SEPHAROSE™ at pH 7.0-8.5 is the most effective. The pH is more preferably about 7.5 or 8.0, and most preferably about 8.0.

The virus may also be purified based on the difference in size, for example, with size exclusion chromatography. For reovirus, a combination of ion exchange and size exclusion chromatography is particularly effective. Preferably, an anion exchange column is used prior to size exclusion chromatography. It is also preferable to avoid magnesium salts in the binding/elution buffers. The use of phosphate buffers rather than Tris-based buffers improved binding and selectivity. Other chromatographic methods, such as those based on affinity or hydrophobic interaction, can also be used where appropriate. Therefore, column chromatography can be adopted as an effective alternative to CsCl density gradient ultracentrifugation to achieve good yield, purity and scalability.

The present method can be applied to reovirus production using cells other than HEK 293 cells, including but not limited to, mouse L929, Vero and Chinese hamster ovary cells. It is contemplated that the present method be applied to other viruses as well, particularly the other non-enveloped viruses. Appropriate conditions for the purification of other viruses can be determined by a person of ordinary skill in the art based on the disclosure herein. The viruses that can be prepared using the present method include, but are not limited to, the viruses in the families of myoviridae, siphoviridae, podpviridae, teciviridae, corticoviridae, plasmaviridae, lipothrixviridae, fuselloviridae, poxviridae, iridoviridae, phycodnaviridae, baculoviridae, herpesviridae, adnoviridae, papovaviridae, polydnaviridae, inoviridae, microviridae, geminiviridae, circoviridae, parvoviridae, hepadnaviridae, retroviridae, cyctoviridae, reoviridae, birnaviridae, paramyxoviridae, rhabdoviridae, filoviridae, orthomyxoviridae, bunyaviridae, arenaviridae, leviviridae, picornaviridae, sequiviridae, comoviridae, potyviridae, caliciviridae, astroviridae, nodaviridae, tetraviridae, tombusviridae, coronaviridae, glaviviridae, togaviridae, and barnaviridae.

Compositions

Also provided are compositions comprising the virus prepared according to methods of the present invention. These compositions can be used in the isolation and characterization of viral proteins, production of vaccines, or, where the composition contains infectious virus, as virus stocks or in clinical administration.

For the purpose of clinical administration, the composition is usually mixed with an excipient, diluted by an excipient or enclosed within a carrier which can be in the form of a capsule, sachet, paper or other container (WO99/08692A1) as a pharmaceutical composition. When the pharmaceutically acceptable excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, sterile saline, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

The route by which the reovirus is administered, as well as the formulation, carrier or vehicle, will depend on the location as well as the type of the target cells. A wide variety of administration routes can be employed. For example, for a solid neoplasm that is accessible, the reovirus can be administered by injection directly to the neoplasm. For a hematopoietic neoplasm, for example, the reovirus can be administered intravenously or intravascularly. For neoplasms that are not easily accessible within the body, such as metastases, the reovirus is administered in a manner such that it can be transported systemically through the body of the mammal and thereby reach the neoplasm (e.g., intravenously or intramuscularly). Alternatively, the reovirus can be administered directly to a single solid neoplasm, where it then is carried systemically through the body to metastases. The reovirus can also be administered subcutaneously, intraperitoneally, intrathecally (e.g., for brain tumor), topically (e.g., for melanoma), orally (e.g., for oral or esophageal neoplasm), rectally (e.g., for colorectal neoplasm), vaginally (e.g., for cervical or vaginal neoplasm), nasally or by inhalation spray (e.g., for lung neoplasm). Preferably, the reovirus is administered by injection.

The liquid forms in which the pharmaceutical compositions of the present invention may be incorporated for administration orally or by injection include aqueous solutions, suitably flavored syrups, aqueous or oil suspensions, and flavored emulsions with edible oils such as corn oil, cottonseed oil, sesame oil, coconut oil, or peanut oil, as well as elixirs and similar pharmaceutical vehicles.

For preparing solid compositions such as tablets, the principal active ingredient/reovirus is mixed with a pharmaceutical excipient to form a solid preformulation composition containing a homogeneous mixture of a compound of the present invention. When referring to these preformulation compositions as homogeneous, it is meant that the active ingredient is dispersed evenly throughout the composition so that the composition may be readily subdivided into equally effective unit dosage forms such as tablets, pills and capsules.

The tablets or pills of the present invention may be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described herein. Preferably the compositions are administered by the oral or nasal respiratory route for local or systemic effect. Compositions in preferably pharmaceutically acceptable solvents may be nebulized by use of inert gases. Nebulized solutions may be inhaled directly from the nebulizing device or the nebulizing device may be attached to a face mask tent, or intermittent positive pressure breathing machine. Solution, suspension, or powder compositions may be administered, preferably orally or nasally, from devices which deliver the formulation in an appropriate manner.

Another preferred formulation employed in the methods of the present invention employs transdermal delivery devices ("patches"). Such transdermal patches may be used to provide continuous or discontinuous infusion of the reovirus of the present invention in controlled amounts. The construction and use of transdermal patches for the delivery of pharmaceutical agents is well known in the art. See, for example, U.S. Pat. No. 5,023,252, herein incorporated by reference. Such patches may be constructed for continuous, pulsatile, or on demand delivery of pharmaceutical agents.

Other suitable formulations for use in the present invention can be found in *Remington's Pharmaceutical Sciences*.

The following examples are offered to illustrate this invention and are not to be construed in any way as limiting the scope of the present invention.

EXAMPLES

In the examples below, the following abbreviations have the following meanings. Abbreviations not defined have their generally accepted meanings.

| | |
|---|---|
| CIP = | cleaning in place |
| CV = | column volume |
| CI = | Confidence Interval |
| ° C. = | degree Celsius |
| DF = | diafiltration |
| DTT = | dithiothrietol |
| FBS = | fetal bovine serum |
| g/L = | grams per liter |
| hr = | hour |
| β-ME = | β-mercaptoethanol |
| μg = | microgram |
| μl = | microliter |
| μM = | micromolar |
| mAU = | milli absorbance units |

-continued

| | |
|---|---|
| mg = | milligram |
| ml = | milliliter |
| mM = | millimolar |
| M = | molar |
| MOI or m.o.i. = | multiplicity of infection |
| NP-40 = | NONIDET ™ P-40 (Octylphenoxy Polyethoxy Ethanol) |
| PBS = | phosphate buffered saline |
| PFU = | plaque forming units |
| rpm = | revolutions per minute |
| SEC = | size exclusion chromatography |
| SDS = | sodium dodecyl sulfate |
| $TCID_{50}$ = | Tissue Culture Infectious Dose 50 |
| UF = | ultrafiltration |

General Materials and Methods (Unless Otherwise Specified)
Cells and Virus

Human embryo kidney 293 (HEK 293) and mouse fibroblast L-929 cells were provided by the manufacturer BioReliance Corporation (Rockville, Md.). HEK 293 cells were grown in a culture medium containing 10% heat-inactivated horse serum and 90% of the following mixture: Eagle's minimum essential medium with 2 mM L-glutamine and Earle's Balanced Salt Solution adjusted to contain 1.5 g/L sodium bicarbonate, 0.1 mM non-essential amino acids, and 1.0 mM sodium pyruvate. Mouse L-929 cells were propagated in a culture medium containing 10% FBS and 90% of the following mixture: Eagle's minimum essential medium with 2 mM L-glutamine and Earle's Balanced Salt Solution adjusted to contain 1.5 g/L sodium bicarbonate, 0.1 mM non-essential amino acids, and 1.0 mM sodium pyruvate.

The 293/SF cells were grown in 293 Serum Free Medium (Life Technologies, Rockville, Md.) supplemented with 4 mM L-glutamine at 36° C.±2° C., 6%±2% $CO_2$ and 80%±5% relative humidity in spinner flasks at an impeller speed of 35-40 rpm.

The Dearing strain of reovirus serotype 3 used in these studies was first propagated in suspension cultures of L-929 cells purified according to Smith (Smith et al., 1969) with the exception that β-mercaptoethanol (β-ME) was omitted from the extraction buffer. The particle/PFU ratio for purified reovirus was typically 100/1. Viral titers were determined by plaque titration on L-929 cells and expressed as $Log_{10}$ $TCID_{50}$/ml. The virus was then produced in large scale in 293/SF cells.

Infection of Suspension Cells

293/SF cells were grown to $10^6$/ml and infected with the reovirus. The culture was allowed to grow until the color of the medium turned from red to orange, or until the viability of the cells dropped to the desired level as evidenced by a viable cell count. Viable cell counts can be performed under the microscope for cells that do not show a cytopathic effect, which is indicated by the cells becoming swollen and granular in appearance and the cell clumps breaking apart. Viable cell counts can also be performed by a viable stain as commonly used in the art.

When the desired cell viability level was reached, the cells were pelleted in a centrifuge and resuspended in 10 mM Tris, pH 7.4, 250 mM NaCl and 0.1% TRITON®X-100. The cells were then lysed by freeze-thawing and kept on ice for 20-40 minutes with periodical vortexing to mix and lyse the cells. The suspension was extracted with an equal volume of pre-chilled FREON® (1,1,2-trichloro-1,1,2-trifluoro-ethane) by vortexing for 10 minutes, followed by centrifugation at 2500 rpm for 10 minutes at 4° C. to separate the difference phases. The aqueous (top) phase was removed and re-extracted twice as described above, and the virus was pelleted by ultracentrifugation at 25,000 rpm for one hour at 4° C.

Traditional Method of Extraction and Purification of Virus

The pellet was resuspended in PBS and the virus was purified by a cesium chloride step gradient. The gradient contained two layers of CsCl solutions (1.20 g/ml and 1.4 g/ml, respectively) prepared in 10 mM Tris (pH 7.4). The virus suspension was loaded on top of the gradient and centrifuged in a SW 28.1 rotor at 26,000 rpm for 2 hours at 4° C. The viral band (the lower of the two bands because the upper band contained empty capsids) was harvested and dialyzed against sterile PBS.

BENZONASE® Endonuclease Treatment

After lysing the cells with a detergent, a solution of 50 mM $MgCl_2$ was added to the crude lysate to a final concentration of 1 mM $MgCl_2$. BENZONASE® endonuclease (250,000 units/ml, EM Industries Catalog No. 1016979M) was then added to approximate 10 units/ml. The lysate was agitated in an incubator at 36° C. for an hour.

Example 1

Clarification: Removing Cell Debris

The purpose of this Example was to develop a suitable clarification procedure that is both compatible with the protocol using detergents to lyse cells and amenable to future scale-up and manufacturing. In this Example, the lysate was filtered either through a 3 μm/0.8 μm capsule filter or passed through a combination of a pre-filter (5 μm or 8 μm) and then a 3 μm/0.8 μm capsule filter. All the filters used in this study had a surface area of 0.015 $ft^2$. Based on the volume filtered through the 0.015 $ft^2$ membrane, the capacity of the membranes was determined for large-scale filtration. Also, filtration efficiency was compared for two different membrane materials—cellulose acetate and glass fiber membrane for the 3 μm/0.8 μm capsule filter.

Three detergents were tested. Reovirus-harboring cells were divided equally into three sterile 1 L bottles labeled for the three different lysis agents to test: 1% TRITON® X-100, 0.3% TRITON® X-100 and 0.1% Na-DOC. A volume of 92 mL and 28 mL of 10% TRITON® X-100 was added to bottles 1 and 2 so that the working concentrations in these bottles were 1% and 0.3% TRITON® X-100, respectively. A volume of 9.2 mL of 10% Na-DOC was added to the third bottle to a working concentration of 0.1%. All the three bottles were placed on a stir plate and agitated at 160±20 rpm for 30 minutes at room temperature. A post-lysis sample was taken for each lysis condition for titer analysis.

About 20 mL of 50 mM $MgCl_2$ was added to the crude lysate in each of the bottles to a working concentration of approximately 1 mM $MgCl_2$. This was followed by addition of 40 μL BENZONASE® endonuclease (250,000 units/mL) to a working concentration of approximately 10 units/mL. The crude lysate was agitated at setting 5 in an incubator at 36° C. for one hour. These steps were included to remove host cell DNA and to reduce viscosity of the lysate, thereby facilitating ease of further processing.

The Watson-Marlow pump (505U) was calibrated to relate flow rate to the pump speed. According to suggestions by the vendor, a pump speed of 5 rpm (40 mL/min flow rate) was used throughout the clarification study.

The lysate from each treatment condition was passed through one of the following filters:
1) 3 μm/0.8 μm capsule filter;
2) A pre-filter 5 μm size→3 μm/0.8 μm capsule filter connected in series; and
3) A pre-filter of 8 μm membrane pore size 3 μm/0.8 μm capsule filter connected in series.

The 3 μm/0.8 μm capsule filters have a double layer heterogeneous membrane construction that allows for high dirt loading capacity and increased throughput. The first filter is of a larger pore size (3 μm) than the second filter (0.8 μm). The pre-filters combine multiple layers of progressively finer pleated non-woven polypropylene depth filter material. All the filters used in this study had a surface area of 0.015 $ft^2$. Two membrane materials, namely cellulose acetate and glass fiber, were tested for the 3 μm/0.8 μm capsule filters.

The best combination of lysis agent and filter conditions was determined based on titer values and the volumes passed through the filters. Pressure drop across the membranes was monitored to determine when membrane fouling occurred. The indication for membrane fouling was a pressure drop of 25 psi, beyond which the filter can break. When the 3 μm/0.8 μm capsule filter was used alone, no more than 35 mL passed through these capsule filters before the membrane fouled. Membrane size 3/0.8 μm fouled within 5 minutes, suggesting that use of a pre-filter was necessary to eliminate clotting of the membranes by cellular debris. Use of a 5 μm pre-filter before the 3/0.8 μm capsule filter significantly increased the amount of filtrate obtained, while filtration through a 8 μm pre-filter followed by 3 μm/0.8 μm capsule filtration gave the highest membrane capacity in terms of volume passed through the filters (an average of 200 mL was collected per 0.015 $ft^2$ of filter surface area). 1% TRITON® X-100 gave the best results compared to the other two lysis conditions.

The results also show that the cellulose acetate membrane material worked better than the glass fiber membrane, based on the volume filtered through these membranes. No significant loss of infectivity was observed at any stage of filtration when compared to infectivity of the bulk harvest (cell culture before lysis and filtration). Based on the results from this study, a 20 L bulk harvest would require 1.5 $ft^2$ of membrane surface area for filtration.

Example 2

Concentration

To select a suitable system to concentrate and diafilter the clarified lysate, a Plate and Frame cassette (Pall Filtron, Northborough, Mass.) and a Hollow Fiber cartridge (A/G Technology, Needham Mass.) were compared. The same polyethersulfone membrane material was used in both systems. The criteria for selection were the ease of use, extent of concentration achieved and the virus titer of the product.

The Plate and Frame cassette used in this study was Pall's MINIM system, which is a laboratory benchtop unit, and the LV Centramate containing two suspended screen channel 300 kD Ultrafiltration Membranes (0.2 $ft^2$ each). Prior to concentrating the clarified lysate, the apparatus was rinsed with 2 L of Reverse Osmosis (RO) water (USP grade) to flush out the storage gel. The cassettes were sanitized with 2 L of warmed 0.1N NaOH. The system was then drained, rinsed with 2 L of RO water and conditioned with the growth medium for the virus. The whole system was drained and the hold-up volume of the system and tubing was determined to be 6 mL.

The Hollow Fiber cartridge tested in this study was A/G Technology's QUIXSTAND™ Benchtop System, Size 4M column Ultrafiltration Cartridge (650 $cm^2$ surface area). As with Plate and Frame cassette, the apparatus was first flushed with 2 L of Reverse Osmosis (RO) water (USP grade) to flush out the storage gel. The cassettes were sanitized with 2 L of warmed 0.1N NaOH. The system was then drained, rinsed with 2 L of RO water and conditioned by flushing with the growth medium of the virus. A constant Feed Flowrate of 600 mL/min was used throughout the experiment.

For both systems, the clarified lysate was recirculated until the material was concentrated to about 250 mL (10 times concentration), and a sample was taken for titer analysis (Post I-Concentration). The concentrate (retentate) was diafiltered against 1 L (5 diafiltration volumes) of Diafiltration Buffer (20 mM Tris+0.2M NaCl+1 mM MgCl$_2$, pH 8.0±0.1), and another sample was taken for titer analysis (Post-Diafiltration). The retentate was further concentrated to about 120 mL. Following the final concentration, the product was drained from the system and collected in a single, sterile container (Post-final Concentration). The system was then rinsed with 40 mL of Diafiltration Buffer to ensure maximum product recovery.

The process parameters monitored during the concentration process with both the hollow fiber and plate and frame systems are shown in Table 1.

About 20 fold-concentration was achieved with the Plate and Frame cassette in 4 hours, while a 14 fold-concentration was obtained using the Hollow Fiber Cartridge in 3 hours and we could have obtained 20 fold-concentration in another 30 minutes. There was 45-50% loss of the product when compared to the post-lysis values with either system. The set-up of the Hollow Fiber Cartridge was easier than the Plate and Frame Cassette. Therefore, the Hollow Fiber Cartridge is a more suitable system for ultrafiltration and diafiltration steps based on ease of handling.

Example 3

Ion Exchange

Viruses have different surface charges due to their different surface molecules. Therefore, it is possible to purify viruses using ion exchange chromatography, and the conditions will vary depending on the nature of the viruses. Accordingly, we tested ion exchange chromatography conditions of various pHs for reovirus purification. Reovirus was produced, extracted and filtered as described above and subjected to ion exchange chromatography at different pH. The titer after each step was determined and is set forth below in Table 2.

TABLE 1

Comparison of Process Parameters for the Hollow Fiber and Plate and Frame Systems

| System | Process Time (hr) | Surface Area (cm$^2$) | Concentration Factor | Average Feed Flow rate (mL/min) | | Permeate Flow Rate ml/min | | TMP (psi) | |
|---|---|---|---|---|---|---|---|---|---|
| | | | | start | end | start | end | start | end |
| Hollow Fiber | 3 | 650 | 14× | 600 | 600 | 50 | 18 | 8 | 8 |
| Plate and Frame | 4 | 372 | 20× | 260 | 450 | 54 | 12 | 9.2 | 30 |

TMP = [(Feed Pressure + Retentate Pressure)/2 − Permeate Pressure]

The Transmembrane Pressure (TMP) stayed at less than 8 psi throughout the hollow fiber process, while the TMP rose to 30 psi with the plate and frame process. The use of more membrane surface area for the hollow fiber system probably resulted in less fouling of the cartridge.

TABLE 2

The effects of ion exchange chromatography at various pH

| Sample | Titer ± 95% CI (Log$_{10}$TCID$_{50}$/ml) | Volume Correction[2] | Corrected Titer ± 95% CI (Log$_{10}$TCID$_{50}$/ml) |
|---|---|---|---|
| Spiking Virus Control, 10/30/01 | 8.05 ± 0.47 | — | — |
| Certified Titer of RE3013101P | 8.35 ± 0.27 | — | — |
| Negative Control | No virus detected | — | — |
| ONC 101, Bulk harvest | ** | — | — |
| ONC 102, Post filtration | 9.18 ± 0.36 | — | 9.18 ± 0.36 |
| ONC 103, Post Column, Strong Cation pH 4.0 | 5.93 ± 0.24 | 1.02 | 5.94 ± 0.24 |
| ONC 104, Post Column, Strong Cation pH 5.0 | 8.93 ± 0.42 | 1.01 | 8.93 ± 0.42 |
| ONC 105, Post Column, Strong Cation pH 6.0 | 9.18 ± 0.40 | — | 9.18 ± 0.40 |
| ONC 106, Post Column, Strong Cation pH 7.0 | 9.30 ± 0.37 | — | 9.30 ± 0.37 |
| ONC 107, Post Column, Strong Cation pH 8.0 | 9.55 ± 0.32 | — | 9.55 ± 0.32 |
| ONC 108, Post Column, Weak Cation pH 4.0 | 8.93 ± 0.40 | 1.01 | 8.93 ± 0.40 |
| ONC 109, Post Column, Weak Cation pH 5.0 | 9.18 ± 0.36 | 1.01 | 9.18 ± 0.36 |
| ONC 110, Post Column, Weak Cation pH 6.0 | 8.68 ± 0.40 | — | 8.68 ± 0.40 |
| ONC 111, Post Column, Weak Cation pH 7.0 | 9.30 ± 0.37 | — | 9.30 ± 0.37 |
| ONC 112, Post Column, Weak Cation pH 8.0 | 8.18 ± 0.36 | 1.02 | 8.19 ± 0.36 |
| ONC 113, Post Column, Strong Anion pH 5.0 | 5.30 ± 0.37 | 1.01 | 5.30 ± 0.37 |
| ONC 114, Post Column, Strong Anion pH 6.0 | 4.80 ± 0.00 | — | 4.80 ± 0.00 |
| ONC 115, Post Column, Strong Anion pH 7.0 | 7.80 ± 0.35 | — | 7.80 ± 0.35 |
| ONC 116, Post Column, Strong Anion pH 8.0 | 10.18 ± 0.36 | 1.01 | 10.18 ± 0.36 |
| ONC 117, Post Column, Strong Anion pH 9.0 | 8.55 ± 0.32 | — | 8.55 ± 0.32 |
| ONC 118, Post Column, Weak Anion pH 5.0 | 7.93 ± 0.40 | — | 7.93 ± 0.40 |
| ONC 119, Post Column, Weak Anion pH 6.0 | 6.68 ± 0.40 | — | 6.68 ± 0.40 |
| ONC 120, Post Column, Weak Anion pH 7.0 | 8.30 ± 0.37 | 1.02 | 8.31 ± 0.37 |

TABLE 2-continued

The effects of ion exchange chromatography at various pH

| Sample | Titer ± 95% CI (Log$_{10}$TCID$_{50}$/ml) | Volume Correction[2] | Corrected Titer ± 95% CI (Log$_{10}$TCID$_{50}$/ml) |
|---|---|---|---|
| ONC 121, Post Column, Weak Anion pH 8.0 | 10.53 ± 0.36 | 1.03 | 10.54 ± 0.36 |
| ONC 122, Post Column, Weak Anion pH 9.0 | 8.93 ± 0.24 | 1.03 | 8.94 ± 0.24 |

Accordingly, pH 7.0-9.0 resulted higher yield of reovirus than other pHs. The pH used in this step is preferably 7.5-8.5, particularly pH 8.0. Although both cation and anion exchangers worked, anion exchangers were generally more effective.

Example 4

Scaleable Purification Protocol

Reovirus is an enterovirus that specifically infects cells with an activated ras-pathway. As the activation of the ras-pathway is a common denominator in a wide variety of cancer types, reovirus serotype 3 has been shown to cause regression in a variety of tumors in cell line, animal models as well as in the clinic. To meet the demands of producing infectious virus at large scale for clinical phase II/III trials a filtration and chromatography based approach was developed. We report here the development of a fully scaleable process for the purification of active virus from cell culture. The three step process consists of an ultrafiltration step, an anion exchange purification and a group separation into formulation buffer. The process was scaled-up to a 20 liter bioreactor scale and transferred to production in a GMP facility. The overall recovery of the process is >50% and the final purity matches material produced by two sequential cesium chloride centrifugation steps.

Materials and Methods

Chromatography: All purification experiments were run on an Äkta Explorer 100 system and fractions were collected via fraction collector Frac 950. UV at 280, 260 and 215 nm as well as conductivity and pH were routinely monitored. All chromatography media and instrumentation was obtained from GE Healthcare, Biosciences.

SDS PAGE: All SDS PAGE materials were obtained from Invitrogen. 4-12% SDS PAGE gels were used and run according to manufacturer's instructions. All samples were denatured for 10 minutes at 65° C. prior to electrophoresis.

Full length rainbow marker was used as a sizing standard (GE Healthcare, Biosciences).

Staining of SDS PAGE: Silver staining reagents were obtained from GE Healthcare Biosciences. Colloidal coomassie stain was obtained from Invitrogen. Manufacturer's instructions were followed for each of the staining reagents. The development step of the silver stain was held for 8 minutes to overstain the gel to ensure that remaining contaminants could be seen clearly.

Western blotting: SDS PAGE gels were run in duplicate so that one of the gels could be transferred to ECL Nitrocellulose. With the exception of the transfer buffer (Invitrogen) all reagents and blotting apparatus were obtained from GE Healthcare Biosciences. The gels were blotted for 40 minutes at 45 V at 20% methanol. Completeness of transfer was checked by transfer of the stained marker. Membranes were blocked in non-fat milk (local grocery store) overnight and incubated with a polyclonal goat antibody diluted 1:20000 in non-fat milk 0.2% Tween. Blots were rinsed 3×5 minutes with excess PBS-Tween 0.2% and then incubated with a monoclonal anti-goat-HRP antibody (Sigma) at 1:100000. Blots were rinsed as described above and then developed with ECL detection reagent according to manufacturer's instructions. The blots were then exposed to Kodak BioMax Light film for 30 seconds, 1 minute, 5 minutes etc. and film was developed manually with GBX developer and fixative (Kodak) according to manufacturer's instructions.

RNA isolation: Samples were prepared for RT-PCR by extraction of RNA from a 0.5 ml sample of each fraction with RNAWizard (Ambion). The manufacturer's protocol was followed and RNA pellets were resuspended in DEPC treated water to a final volume of 0.1 ml. 1 ml of each sample as well as a 1:10 dilution were used for amplification by RT-PCR.

Agarose gel electrophoresis of PCR samples: PCR reactions were analyzed on a 4% EZ gel (Invitrogen) by adding 20 ml of a 6× loading dye containing VistraGreen (GE Healthcare, Biosciences) at a 1:10000 dilution and 50% glycerol. 20 ml were applied per well and a 50 bp ladder (GE Healthcare, Biosciences) was used as a sizing standard.

Detection of PCR bands: All gels were scanned on a Typhoon 9600 scanner at Ethidium Bromide settings at 650 PMT setting and normal sensitivity setting at 50 micron resolution.

Sepharose, ÄKTAexplorer, Unicorn, HR, ImageQuant, Vistra Green and Typhoon are trademarks of GE Healthcare. GE Healthcare is a trademark of General Electric.

E-gel and Novex gels are registered trademarks of Invitrogen Corp. The Polymerase Chain Reaction (PCR) is covered by patents owned by Roche Molecular Systems and F. Hoffman-La Roche Ltd.

Process Development: Description of the Starting Material

Reovirus is a non-enveloped, double-stranded RNA virus with an icosahedral symmetry and a well known protein composition. It has a diameter of ~85 nm and a molecular weight of ~126 million dalton. The outer capsid which will determine binding behavior of the virus to chromatography matrices consists of 600 copies of the major outer capsid protein λ1 with a molecular weight of 76.3 kDa, 600 copies of major outer capsid protein σ3 where the outer capsid building blocks are actually made up of heterohexamers of μ1σ3. In addition 36 copies of the minor outer capsid protein σ1 are also found on the virus surface as homotrimers. σ1 mediates viral attachment to the cell surface. The three outer capsid proteins σ3, σ1 and μ1 have isoelectric points of 5.2, 5.2, and 6.6 respectively. The inner capsid consists of 120 copies of λ1 (dimers), 60 copies of λ2 (as pentamers) and 24 copies of μ1. The core consists of 12 copies of λ3, the RNA polymerase and 120 copies of σ2, the major core protein. All λ proteins have molecular weights of approximately 120 kDa, μ of approximately 80 kDa and σ of approximately 47-48 kDa.

All material used for process development was generated as follows. A 20 liter bioreactor was inoculated with an HEK 293 derived cell line in serum free medium containing 4 mM glutamine and phenol red. Cells were grown for 2-3 days and infected at a cell count of 1×10$^6$ cells/ml with an MOI of 0.5.

Virus production was allowed to proceed for another 2-3 days. The cells were lysed by addition of 10% Triton X-100 to a final concentration of 1% at 37° C. for 30 minutes at 120 rpm. The sample concentration of the crude lysate was adjusted to 1 mM Magnesium Chloride and digested with benzonase at 10 u/ml for 1 hour at 37° C. and 120 rpm. The material was then filtered through an 8 micron filter followed by a 0.8 micron filter. The material was further concentrated and buffer exchanged on a GE Healthcare Hollow Fiber cartridge with a molecular weight cut-off of 300 kDa and a total area of 4800 cm$^2$. The material was exchanged against 5 volumes of 20 mM Tris buffer pH 7.8, 25 mM sodium chloride. After diafiltration, glycerol was added to a final concentration of 10%.

Parameters to Determine an Acceptable Working Range for Reovirus Purification

A stability window for the purification of reovirus type 3 Dearing was indicated by the following references (Floyd et al., 1977; Floyd et al., 1978 p. 1079-1083 and 1084-1094; Floyd et al., 1979; Drayna et al., 1982). Based on the literature it was assumed the chromatography conditions over a pH range of 5.0-8.0 and at salt concentrations from 0-2 M sodium chloride would be a good starting range. Aggregation and conditions that could potentially induce aggregation were also factors to be considered. Based on the data from the literature (id.), it was assumed that a pH window from pH 5.0-8.0 and salt concentrations from to 0.025-2 M sodium chloride would be acceptable. Glycerol was also added to all buffers to prevent aggregation. Whether omission of glycerol would have a detrimental effect on viral stability and infectivity due to loss of virus by aggregation was not tested.

The isoelectric point (pI) of the virion has been described in the literature (Floyd et al., 1978 p. 1084-1079, Taylor et al., 1981). An apparent pI of 3.8-3.9 has been indicated using chromatofocusing and whole-particle microelectrophoresis. The two most abundant major coat proteins of reovirus type 3 Dearing, sigma 3 and mu 1 have a much less acidic pI (see above). This is also in better agreement with the adsorptive behavior of the virus to different ion exchangers (Zerda et al., 1981). The discrepancy is most likely explained by the fact that chromatofocusing is in many respects a 2 dimensional technique measuring charged domains rather than overall charge in solution, whereas microelectrophoresis may produce some deviation by modulation of buffer conditions which may also affect experimental outcome. The use of magnesium salts in buffer formulations was avoided as a decline of virus infectivity upon freezing in the presence of magnesium has been reported (Estes et al., 1979).

Initial Media Scouting

Ion exchange (IEX), hydrophobic interaction chromatography (HIC), heparin affinity chromatography and immobilized metal chelating chromatography (IMAC) were all evaluated initially. σ3, one of the two major outer capsid proteins does contain a zinc finger motif and IMAC was therefore considered as a potential capture technique for this virus.

To determine whether the virions would bind to the different type of chromatography media at all, the virus was also group separated on Sepharose 4 Fast Flow to remove some of the main contaminants and to exchange the virus to buffer conditions more suitable for binding. Both Sepharose 6 and 4 Fast Flow were initially evaluated at bed heights of 20 cm and linear flow rates of 150 cm/h. Sample volumes of 5-30% of the column volume were applied. As the size exclusion limit of Sepharose 6 Fast Flow is in the range of 2-5 million dalton for spherical molecules and Sepharose 4 Fast Flow has an exclusion limit of about 20 million dalton, the latter offered better resolution and hence allowed application of up to 25% of the column volume. Above this value, the peaks could no longer be resolved. This could not be suppressed by addition of salt and or ethylene glycol. A typical chromatogram of a size separation of the starting material on an HR5_20 Sepharose 4 Fast Flow column is shown in FIG. 1.

Figure 2:
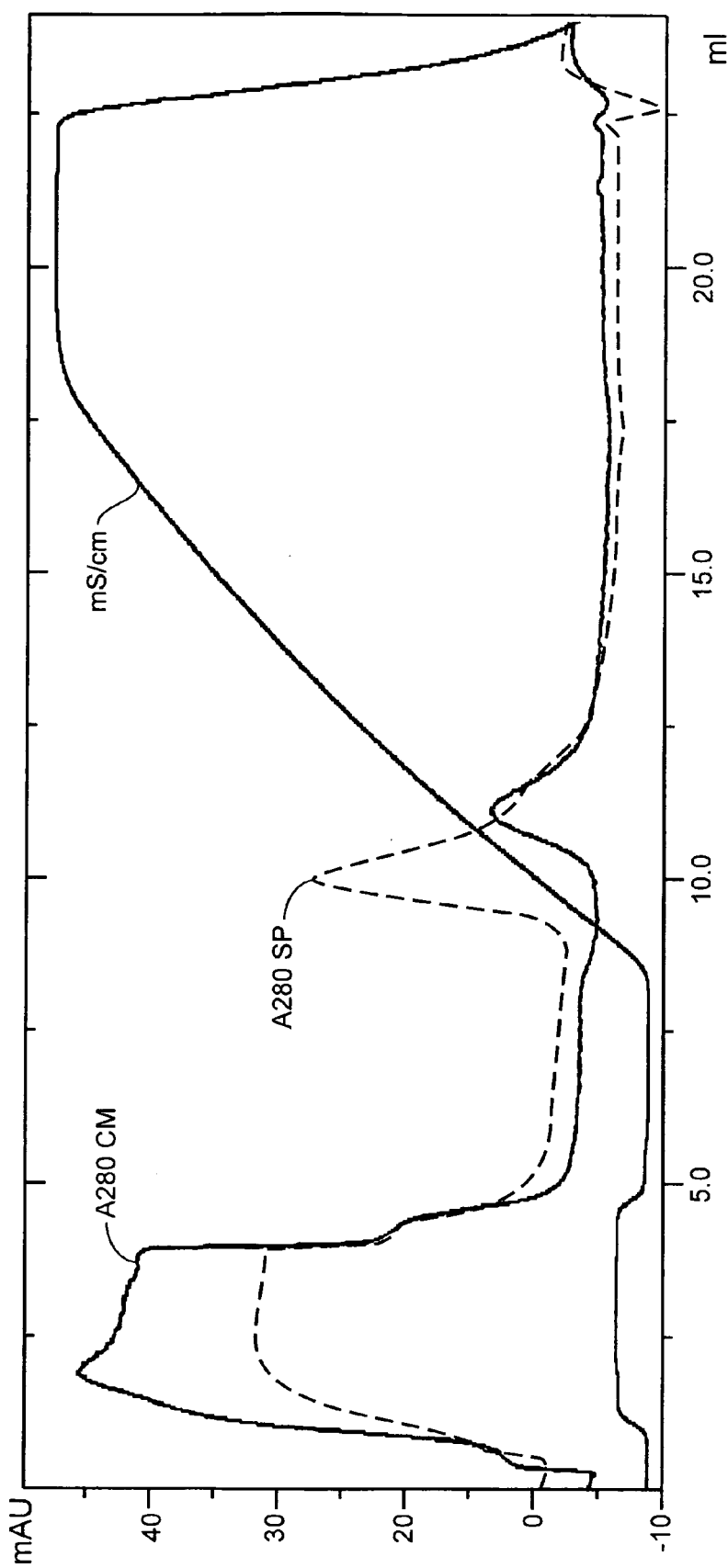
FIG. 2 shows separation of the size exclusion chromatography (SEC) prepurified material on an Äkta Explorer 100 at 50 cm/h. Buffer A: 50 mM Sodium Acetate pH 5.6, 5% Glycerol. Buffer B: A+1 M Sodium chloride. x-axis in ml; y-axis in milli-absorption units at 280 nm. The A280 CM line indicates the elution profile from a 1 ml HiTrap CM Sepharose column, the A280 SP line from a 1 ml HiTrap SP Sepharose column.

Cation exchange media were tested over a pH range of 5.0-6.0. Both weak (carboxymethyl) and strong (sulfopropyl) cation exchange groups were used (FIG. 2).

For the size exclusion prepurified virus, good binding of the virus was observed both on SP and CM Sepharose Fast Flow at pH 5.6. However, the UF/DF material did not bind at all, even at a pH of 5.0. The addition of 2.5% ethylene glycol helped to break up aggregates that had formed and allowed binding of the virus but decreased viral infectivity.

Calcium, Zinc and Magnesium charged chelating metal sepharose was also tested for binding of the virus with SEC pre-purified material. However, at both 25 and 50 cm/h sample application, no virus was retained on the column. Heparin Sepharose 6 Fast Flow was also evaluated at different salt concentrations with prepurified virus, but again, no binding was observed. Fractions were analyzed by RT PCR as described (Spinner et al., 2001) and by Western blotting and SDS PAGE.

While all HIC columns seemed to retain the virus to some extent, selectivity was poor and losses due to precipitation, even when sodium chloride was used as the lyotropic salt, were high.

Figure 3:
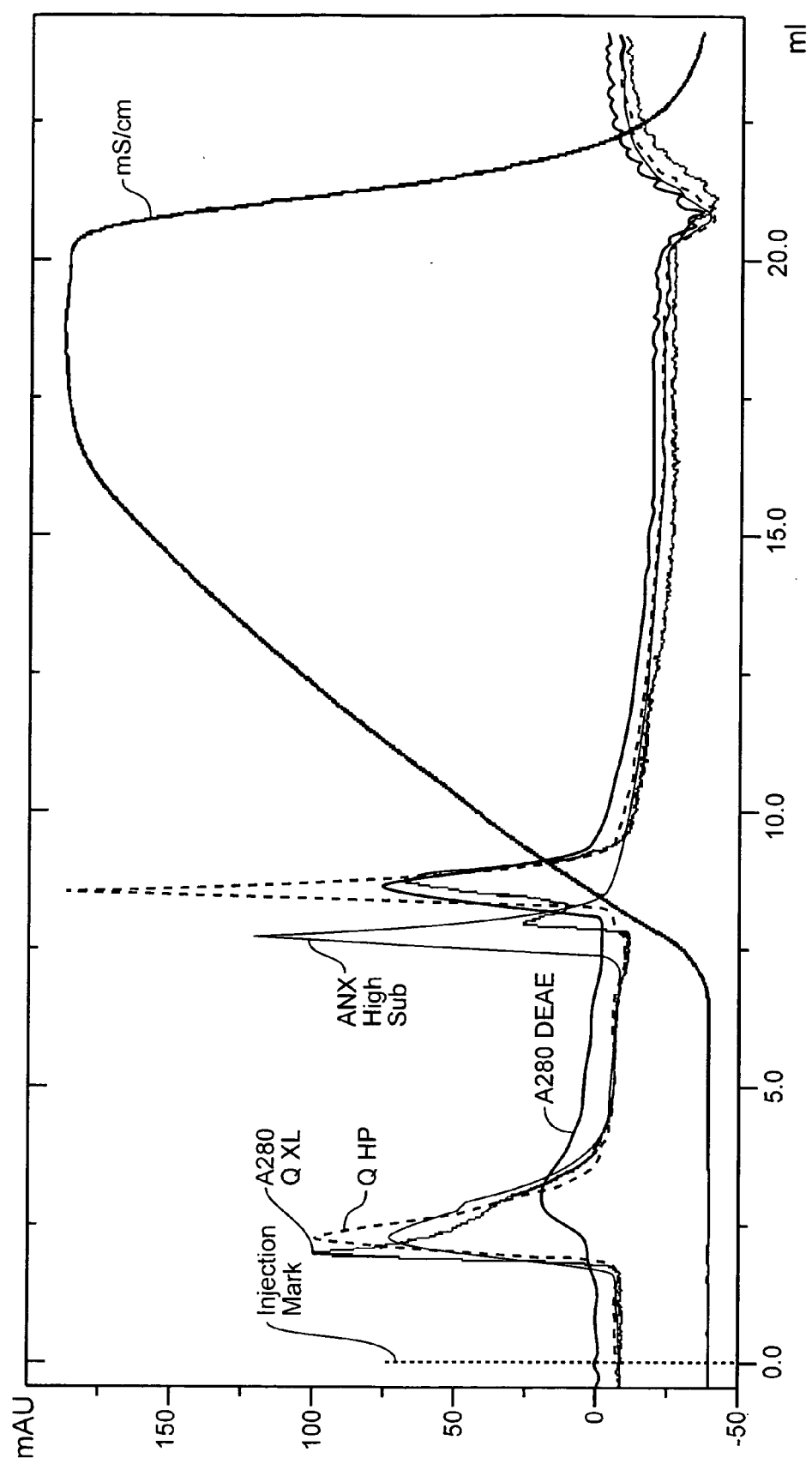
FIG. 3 shows separation of SEC pre-purified reovirus on different HiTrap anion exchange columns. Flow rate; 50 cm/h. Buffer A: 25 mM TrisCl pH 7.2, 5% glycerol. Buffer B: A+1 M sodium chloride. A 10 CV gradient was run to elute the material. x-axis in ml; y-axis in milli-absorption units at 280 nm. Elution profiles as detected by A280 nm were as follows: A280 DEAE=DEAE Sepharose Fast Flow; A280 Q XL=Q Sepharose XL, ANX High Sub=ANX high sub; Q HP=Q Sepharose HP.

Different anion exchangers were also screened for selectivity and binding. DEAE, ANX high sub, Q Sepharose Fast Flow, XL and High Performance (HP) were all evaluated for binding of the virus. Selectivity seemed to differ when the SEC pre-purified material was tested (FIG. 3).

Anion exchange seemed to be the most robust, scaleable choice for a first purification step. Therefore, different anion exchangers were evaluated further for purification of reolysin.

Optimization of the Anion Exchange Capture Step

The different anion exchangers clearly offered different selectivity. Q Sepharose XL was the most markedly different, generating a split viral peak. As the virus is not stable above a pH of 8.0, and the microenvironment of anion exchangers during binding maybe up to 1 pH unit higher, the sample was applied at a pH of 7.2 and all subsequent steps were kept to a pH of 7.0. The sample was adjusted to a pH of 7.2 with dilute hydrochloric acid.

Figure 4:
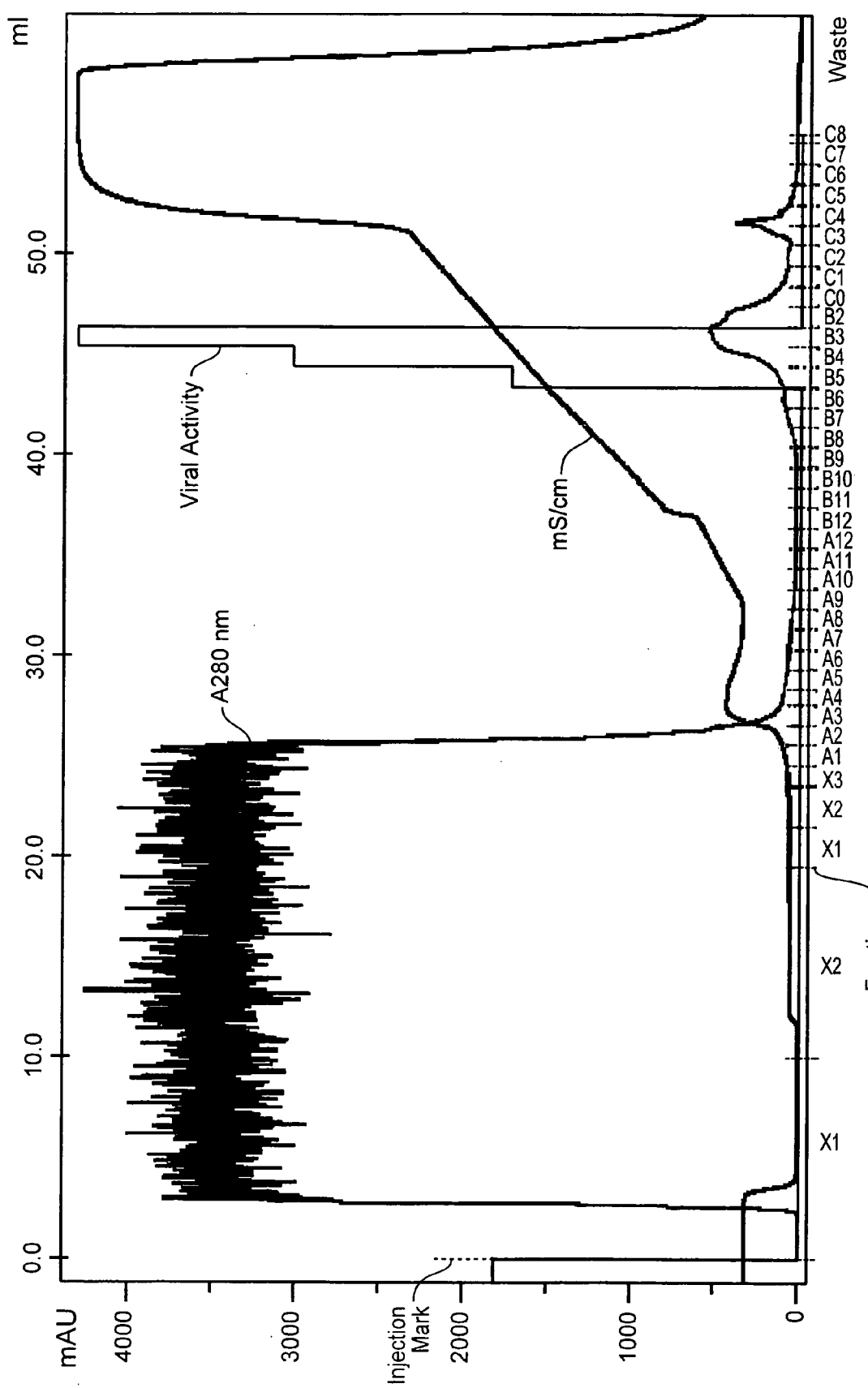
FIG. 4 shows determination of the dynamic binding capacity at 5-10% breakthrough on an HR5__100 Q Sepharose HP column at 50 cm/h. More than 12 CV were applied before breakthrough was observed. Buffer A: 50 mM sodium phosphate pH 7.2, 5% glycerol. Buffer B: 50 mM sodium phosphate pH 7.0, 5% glycerol, 2 M sodium chloride. A 10 CV linear gradient to 1 M sodium chloride was used, followed by a 5 CV step to 2 M sodium chloride. Viral fractions (viral activity) were determined by RT-PCR and Western blotting. Y-axis: A280 nm in mAU, x-axis: volume in ml.

As selectivity in Tris-Cl buffer seemed poor, phosphate buffer was also evaluated. Both binding and selectivity was improved by the use of phosphate buffer (data not shown). The five different anion exchangers were also compared for binding capacity. Early breakthrough was observed for all of the 90 micron beads (ANX high sub, DEAE, Q Fast Flow, and XL) where material did breakthrough after 1-2 column volumes. Q Sepharose High Performance allowed application of more than 12 CV of virus before breakthrough was observed at 5 cm bed height and 50 cm/h linear flow rate or 6 minute residence time (FIG. 4).

Q Sepharose High Performance was therefore chosen for further process development of the first step. Elution of the virus from Q Sepharose HP with a linear gradient to 1 M sodium chloride indicated that the virus eluted at 0.5 M with some residual contaminants eluting earlier in the gradient and some additional contaminants eluting late in the gradient.

Figure 5:
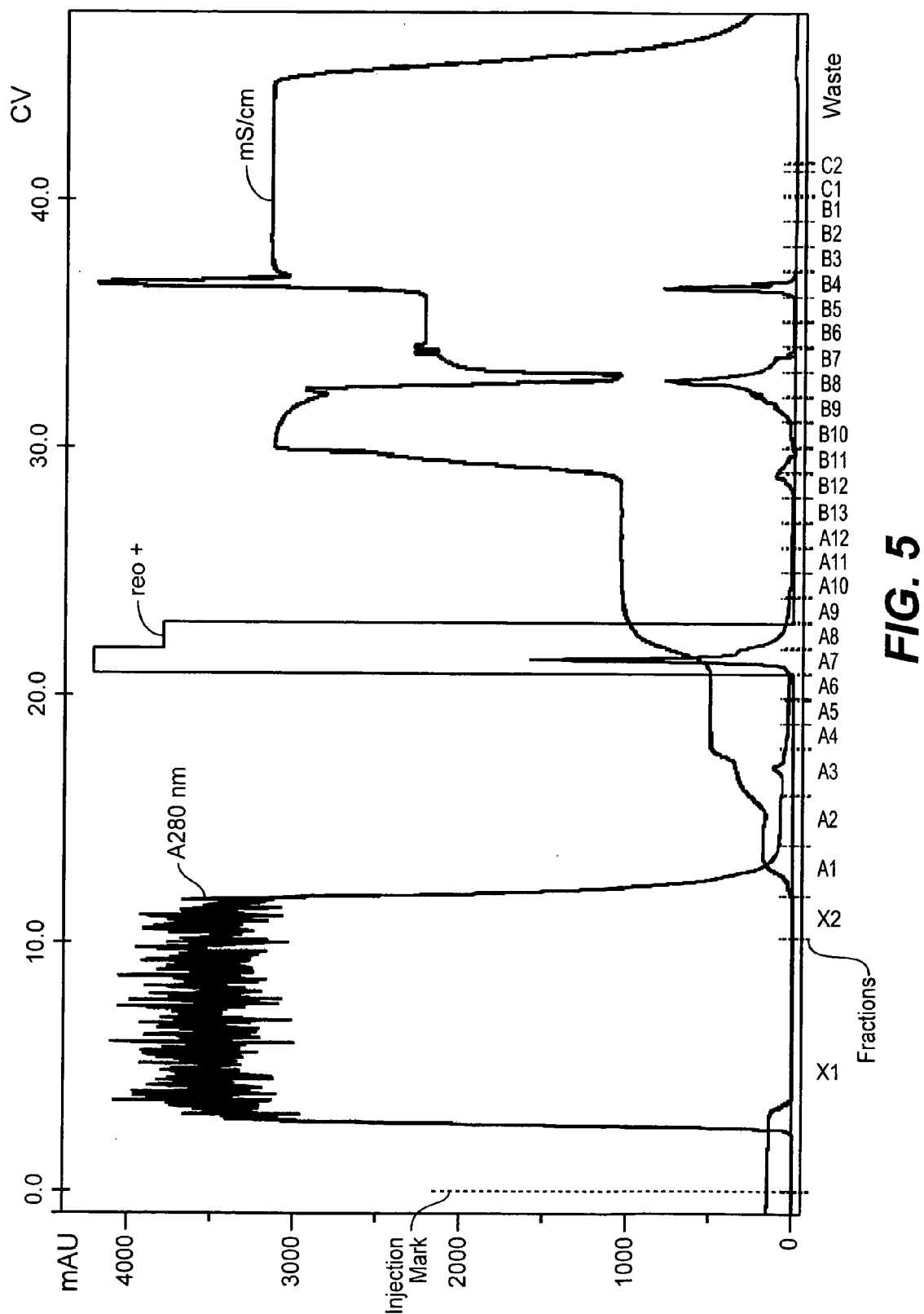
FIG. 5 shows development of a step protocol for easy scale-up of the capture of reovirus on Q Sepharose HP. Purification of 5 CV of UF/DF reovirus adjusted to pH 7.2 with dilute hydrochloric acid on an HR5__100 Q Sepharose HP column connected to an Aekta Explorer 100. Buffer A: 50 mM Sodium Phosphate pH 7.2, 5% Glyercol. Buffer B: 50 mM Sodium Phosphate pH 7.0, 5% Glycerol, 2 M Sodium Chloride. Step gradient: 12.0% B for 5 CV (wash), 25% B for 5 CV (elution), 50% B for 5 CV (regenerate) and CIP for 2 CV (1 M Sodium Hydroxide, followed by 5 CV of 100% B). Y-axis: mAU, x-axis: volume in ml. Virus containing fractions are indicated by reo+.

Different step concentrations for washing, elution and regeneration were evaluated. Optimal conditions were found when the column was washed at 0.24 M sodium chloride (virus did not elute until about 0.26-0.27 M sodium chloride), elution at 0.5 M sodium chloride and regeneration at 2 M sodium chloride (FIG. 5).

The step protocol allowed concentration of the virus by a factor of 8-10×, and both titer as well as Western blotting and RT-PCR indicated recoveries of 60-70%. A cleaning regimen was also developed and a combination of regeneration at 2 M sodium chloride for 2 CV at 50 cm/h followed by 1 M sodium hydroxide for 2 CV at 25 cm/h in up-flow direction, followed by an additional 2 CV of 2 M sodium chloride at 50 cm/h in up-flow allowed full recovery of column capacity and elution profile (data not shown). As viral titers reached were high enough for final formulation, group separation on Sepharose 4 Fast Flow at 150 cm/h and 20 cm bed height was chosen for a second purification and buffer exchange step. Up to 35% of the total column volume could be applied under these conditions and the virus was exchanged into final formulation buffer.

Scale-Up
Eight Fold Scale-Up of the Anion Exchange Purification

Figure 6:
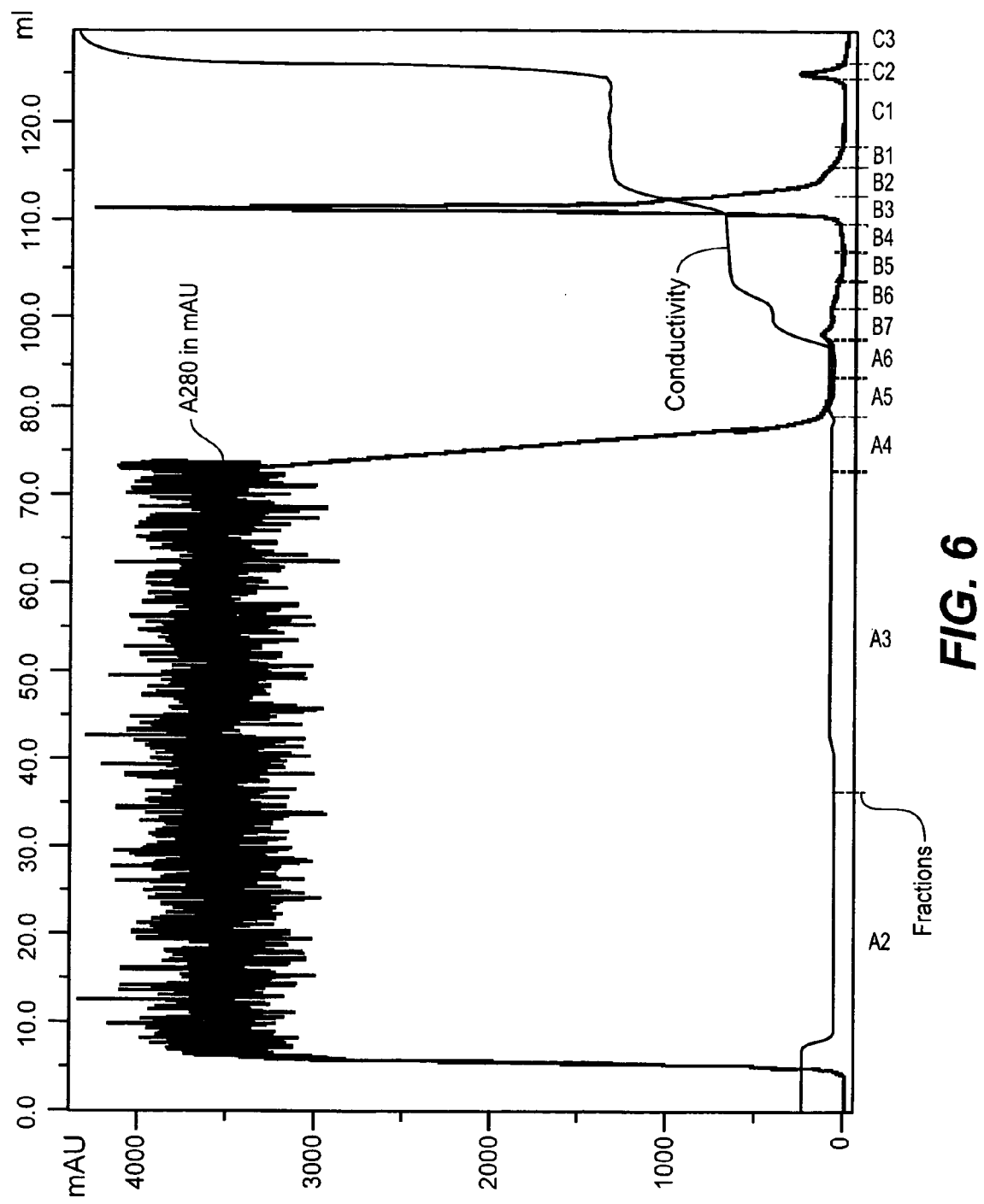
FIG. 6 shows an 8× scale up of the capture of reovirus on Q Sepharose HP. Purification of 10 CV of UF/DF reovirus adjusted to pH 7.2 with dilute hydrochloric acid on an HR10__100 Q Sepharose HP column. Buffer A: 50 mM sodium phosphate pH 7.2, 5% glycerol. Buffer B: 50 mM sodium phosphate pH 7.0, 5% glycerol, 1 M sodium chloride. Step gradient: 12.0% B for 5 CV (wash), 25% B for 5 CV (elution), 50% B for 5 CV (regenerate) and CIP for 2 CV (1 M sodium hydroxide, followed by 5 CV of 100% B). Y-axis: mAU, x-axis: volume in ml. Virus eluted in Fractions B3/2 in a volume of ~5 ml.

To demonstrate scalability, the process was scaled up 8 fold to an HR10__100 Q Sepharose High Performance column. All parameters such as residence time, volumes applied, step concentrations and mg of sample applied/ml of resin were kept constant for scale-up. The elution profile of contaminants as well as the viral peak were almost identical during this 10 fold scale-up (FIG. 6).

The process was scaled up further for a pilot plant and subsequent GMP runs by a factor of 50×. Five liters of a 4× UF/DF prepurified virus were purified with the developed process at comparable recoveries and purity.

Figure 7:
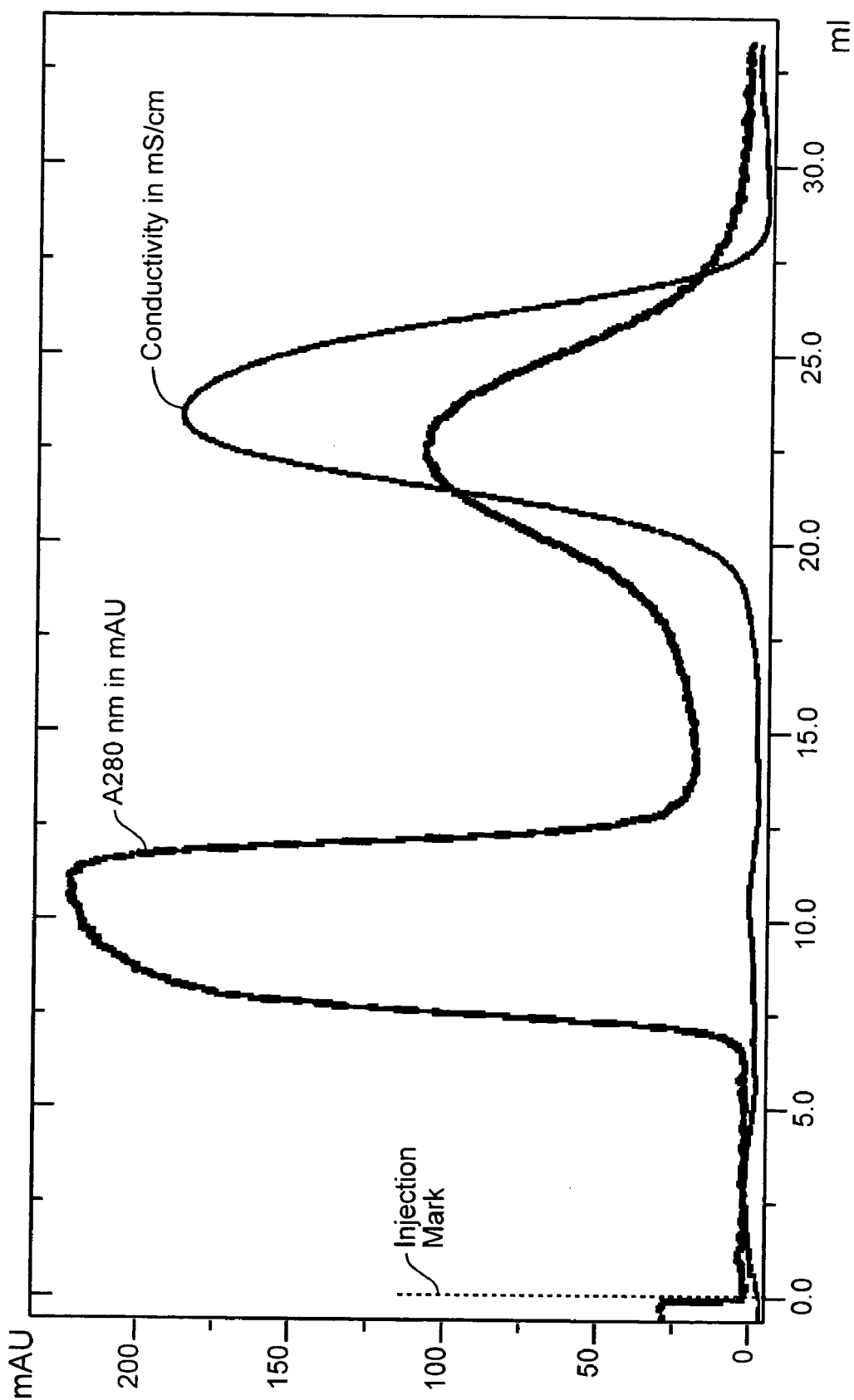
FIG. 7 shows an 8 fold scale up of the second step of the purification of the virus fraction on HR10__200 Sepharose 4 Fast Flow 20 ml column. 0.25 CV applied (fractions B3½ as shown in FIG. 6). Linear flow rate: 150 cm/h. Buffer: PBS, 5% glycerol.

To reach the same final purity level as for the Cesium Chloride gradient purified material, the group separation was also scaled ten fold. The elution profile of the ten fold scale-up of the second step is shown in FIG. 7.

The purity of the final product was comparable to the gradient purified material as shown by Silver stained SDS PAGE (FIG. 8A). The two step procedure also generated material at a higher concentration than the gradient purified material as shown by Coomassie stained SDS PAGE (FIG. 8B). Western blot analysis confirmed the identity of viral bands and allowed quantitation of the virus recovery for the overall process. Overall recovery was >50%. This was also confirmed by the titer assay (FIG. 8C).

Summary of Example 4

A purification process was developed for the purification of a non-enveloped virus and scaled up more than 50 fold. Screening of different chromatographic separation principles indicated that anion exchange and size exclusion are the best choice for purification of a fully biologically active (infectious) virion in the case of reovirus. Conditions for anion exchange and size exclusion chromatography as a first and second step respectively were carefully screened and optimized to allow a robust, scaleable protocol. Special attention was paid to the adsorption and desorption step flow rates for the first step as well as for the sample injection and isocratic elution of the second step. Binding capacity for the different anion exchangers was evaluated, and as only surface binding occurs for particles >2 MDa on 6% agarose media, and >20 MDa on 4% agarose media, use of a smaller bead increased the binding capacity proportionally to the reduction in bead diameter (by a factor of 3 and 9, respectively). The use of phosphate buffer rather than Tris based buffer gave better selectivity when eluting the virus and also seemed superior in terms of recovery of biological activity. Additionally, the use of magnesium salts was avoided in the diafiltration and elution buffers.

An 8 fold scale-up showed that elution profiles were reproducible upon scale-up and that the step protocol allowed recovery of the infectious virus at an about 60-70% yield. The second step was necessary to reach the final purity of virus purified by two consecutive density gradient centrifugation steps and allowed buffer exchange of the virus to the final formulation buffer at the same time. Final titers were high enough to omit an additional ultrafiltration step due to the increased capacity of the Q Sepharose High Performance media. No negative impact due to potential backpressure issues when using a 34 micron bead was observed upon scale-up to a BPG100 column. The pressure drop over the bed remained below 1.5 bar during the entire sample application and protocol.

However, inconsistencies in capacity were observed upon scale-up due to varying amounts of phenol red in different batches of starting materials and when low titer viral starting material was used. Under these conditions some of the viral material was lost in the wash step, and losses could be as high as 50%. However, better control of the quality of the starting material, allowed to recover the performance of the purification process to values comparable to the initial small scale process.

In sum, this invention provides a purification process for large-scale reovirus production of a quality comparable to that of traditional small scale processes.

Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

What is claimed is:

1. A method of producing virus from a culture of cells, comprising the steps of:
    (a) providing a culture of cells which has been infected by the virus;
    (b) extracting the virus from the cells by adding a detergent to the culture of cells and incubating for a period of time to result in a cell lysate;
    (c) removing cell debris;
    (d) collecting the virus; and
    (e) in the absence of magnesium, purifying the virus by resin or bead ion exchange chromatography, size exclusion chromatography, or a combination thereof.

2. The method of claim 1 wherein the cell debris is removed by filtration.

3. The method of claim 1 wherein the cell debris is removed by step-wise filtration comprising:
    (1) filtering through a prefilter having a pore size of 5 µM or 8 µM, and
    (2) filtering after step (1) through a combination filter having pore sizes of 3 µM and 0.8 µM.

4. The method of claim 1 wherein the cell debris is removed by step-wise filtration comprising:
    (1) filtering through a prefilter having a pore size of 5 µM or 8 µM, and
    (2) filtering after step (1) through a filter having a pore size of 0.8 µM.

5. The method of claim 1 further comprising treating the cell lysate with a DNA-cleaving enzyme.

6. The method of claim 2 further comprising concentrating the filtrate.

7. The method of claim 6 wherein the filtrate is concentrated by diafiltration.

8. The method of claim 7 wherein the diafiltration is performed with a hollow fiber cartridge having a molecular weight cut-off of 300 kDa.

9. The method of claim 1 wherein the virus is a non-enveloped virus.

10. The method of claim 1 wherein the virus is a reovirus.

11. The method of claim 10 wherein the reovirus is a mammalian reovirus.

12. The method of claim 11 wherein the mammalian reovirus is a human reovirus.

13. The method of claim 12 wherein the human reovirus is a serotype 3 virus.

14. The method of claim 13 wherein the serotype 3 reovirus is the Dearing strain.

15. The method of claim 10 wherein the reovirus is a recombinant reovirus.

16. The method of claim 1 wherein the cells are human embryo kidney 293 (HEK 293) cells.

17. The method of claim 16 wherein the HEK 293 cells are grown in suspension.

18. The method of claim 1, wherein the resin or bead ion exchange chromatography is resin or bead anion exchange chromatography.

19. The method of claim 1, wherein the virus is purified by resin or bead ion exchange chromatography and size exclusion chromatography.

20. The method of claim 19 wherein ion exchange is performed using an anion exchanger.

21. The method of claim 19 wherein the ion exchange is performed prior to the size exclusion chromatography.

22. The method of claim 19 wherein a phosphate buffer is used in the resin or bead ion exchange chromatography and size exclusion chromatography.

23. The method of claim 22, wherein the phosphate buffer comprises 50 mM sodium phosphate, pH 7.2.

24. A method of producing infectious reovirus, comprising:
  (a) providing a culture of HEK 293 cells which has been infected by reovirus;
  (b) extracting the virus from the cells by adding octoxynol-9 to 10 to the culture and incubating at about 25° C. to about 37° C.;
  (c) treating the mixture from step (b) with a DNA-cleaving enzyme;
  (d) removing cell debris by filtration;
  (e) concentrating the filtrate by ultrafiltration or diafiltration;
  (f) in the absence of magnesium, purifying the reovirus by a combination of resin or bead ion exchange chromatography and size exclusion chromatography; and
  (g) collecting the reovirus.

25. The method of claim 24 wherein step (f) comprises resin or bead anion exchange chromatography followed by size exclusion chromatography.

* * * * *

UNITED STATES PATENT AND TRADEMARK OFFICE
CERTIFICATE OF CORRECTION

| | |
|---|---|
| PATENT NO. | : 7,901,921 B2 |
| APPLICATION NO. | : 11/255800 |
| DATED | : March 8, 2011 |
| INVENTOR(S) | : Matthew C. Coffey |

It is certified that error appears in the above-identified patent and that said Letters Patent is hereby corrected as shown below:

Column 4, lines 4, 5, 7, and 10, each occurrence of "μM" should be changed to --μm--.

Column 10, lines 56, 59, 62, and 63, each occurrence of "μM" should be changed to --μm--.

Column 24, Claim 3, lines 54, 55, and 57, each occurrence of "μM" should be changed to --μm--.

Column 24, Claim 4, lines 60, 61, and 63, each occurrence of "μM" should be changed to --μm--.

Signed and Sealed this
Third Day of May, 2011

David J. Kappos
*Director of the United States Patent and Trademark Office*